US011590220B2

United States Patent
Dai et al.

(10) Patent No.: US 11,590,220 B2
(45) Date of Patent: Feb. 28, 2023

(54) ANTIGENS OF β-CORONAVIRUSES, PREPARATION METHODS AND USES THEREOF

(71) Applicant: INSTITUTE OF MICROBIOLOGY, CHINESE ACADEMY OF SCIENCES, Beijing (CN)

(72) Inventors: Lianpan Dai, Beijing (CN); Jinghua Yan, Beijing (CN); Fu Gao, Beijing (CN); Yan Li, Beijing (CN); Tianyi Zheng, Beijing (CN); Kun Xu, Beijing (CN); Mei Liu, Beijing (CN); Yaling An, Beijing (CN); Yi Shi, Beijing (CN)

(73) Assignee: INSTITUTE OF MICROBIOLOGY, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/827,256

(22) Filed: May 27, 2022

(65) Prior Publication Data

US 2022/0305113 A1    Sep. 29, 2022

Related U.S. Application Data

(63) Continuation of application No. PCT/CN2020/097775, filed on Jun. 23, 2020.

(30) Foreign Application Priority Data

Feb. 10, 2020   (CN) .......................... 202010085038.9

(51) Int. Cl.
| | | |
|---|---|---|
| *A61K 39/00* | (2006.01) | |
| *A61K 39/215* | (2006.01) | |
| *A61K 39/12* | (2006.01) | |
| *A61P 31/14* | (2006.01) | |
| *C07K 16/10* | (2006.01) | |
| *A61K 39/39* | (2006.01) | |
| *C07K 14/005* | (2006.01) | |

(52) U.S. Cl.
CPC ............ *A61K 39/215* (2013.01); *A61K 39/39* (2013.01); *A61P 31/14* (2018.01); *C07K 14/005* (2013.01); *A61K 2039/55505* (2013.01); *A61K 2039/55566* (2013.01)

(58) Field of Classification Search
CPC .................. A61K 39/215; A61K 39/12; C12N 2770/20034; C12N 2770/20022; A61P 31/14
See application file for complete search history.

(56) References Cited

FOREIGN PATENT DOCUMENTS

CN        107033250 A      8/2017

*Primary Examiner* — Barry A Chestnut
(74) *Attorney, Agent, or Firm* — Hauptman Ham, LLP

(57) ABSTRACT

The embodiments of the present disclosure relate to antigens of β-coronaviruses, preparation methods and uses thereof. The amino acid sequence of the antigen of the β-coronavirus includes an amino acid sequence arranged in a (A-B)-(A-B) pattern or an amino acid sequence arranged in a (A-B)-C-(A-B) pattern or an amino acid sequence arranged in a (A-B)-(A-B') pattern or an amino acid sequence arranged in a (A-B)-C-(A-B') pattern. The antigen of the β-coronavirus has a single-chain dimer structure. A single-chain dirtier expressed according to examples of the present disclosure is stable in content and has excellent immunogenicity as an antigen of a β-coronavirus, and a vaccine prepared by using the single-chain dimer as an antigen of a β-coronavirus can elicit high-titer neutralizing antibodies in mice.

21 Claims, 17 Drawing Sheets

Specification includes a Sequence Listing.

FIG. 7

MERS-CoV-RBD dimer (E367-Y606)

FIG. 8

SARS-CoV-RBD dimer / 2019-nCoV-RBD dimer (Model)

RBD molecule 1     RBD molecule 2

| | | |
|---|---|---|
| nCoV-RBD-C1 | R319-S530 | R319-S530 |
| nCoV-RBD-C2 | R319-K537 | R319-K537 |
| nCoV-RBD-C3 | R319-F541 | R319-F541 |
| nCoV-RBD-C4 | R319-F541 | |
| SARS-CoV-RBD-C1 | R306-Q523 | R306-Q523 |

Live SARS-CoV-2 neutralization (2nd immunization)

| Group | Serum ID | NT$_{50}$ |
|---|---|---|
| sc-dimer | 1 | 4096 |
| | 2 | 1024 |
| | 3 | 2048 |
| | 4 | >4096 |
| | 5 | >4096 |
| | 6 | 512 |
| | 7 | 4096 |
| | 8 | 4096 |
| Monomer | 9 | 128 |
| | 10 | 256 |
| | 11 | <16 |
| | 12 | <16 |
| | 13 | <16 |
| | 14 | <16 |
| | 15 | <16 |
| | 16 | <16 |
| PBS | 17 | <16 |
| | 18 | <16 |
| | 19 | <16 |
| | 20 | <16 |
| | 21 | <16 |
| | 22 | <16 |
| | 23 | <16 |
| | 24 | <16 |

ANTIGENS OF β-CORONAVIRUSES, PREPARATION METHODS AND USES THEREOF

CROSS-REFERENCE

This application is a Continuation of International Application No. PCT/CN2020/097775, filed Jun. 23, 2020, and claims priority to Chinese Patent Application No. CN202010085038.9, filed Feb. 10, 2020, with China National Intellectual Property Administration, entitled "ANTIGENS OF β-CORONAVIRUSES, PREPARATION METHODS AND USES THEREOF", which is incorporated herein by reference in its entirety.

TECHNICAL FIELD

The present disclosure relates to the field of biomedical technology, and in particular, to antigens of β-coronaviruses, preparation methods and uses thereof.

INCORPORATION BY REFERENCE

The sequence listing provided in the file entitled Revised_Sequence_Listing_2022-05-27.txt, which is an ASCII text file that was created on May 27, 2022, and which comprises 48,759 bytes, is hereby incorporated by reference in its entirety.

BACKGROUND ART

Coronaviruses, belonging to the coronavirus genera of the family *Coronaviriciae*, are positive-strand enveloped RNA viruses, the genome of which is the largest among all RNA viruses. Both animals and humans can be hosts of coronaviruses. Coronaviruses mainly infect the respiratory tracts and digestive tracts of mammals and birds, and seven kinds of coronaviruses are currently known to infect humans, including four (HCoV-229E, HCoV-NL63, OC43 and HKU1) that may cause a mild cold. Globally, there are three kinds of coronaviruses imposing the greatest threats to public health, namely severe acute respiratory syndrome coronavirus (SARS-CoV) that broke out in 2002-2003, Middle East respiratory syndrome coronavirus (MERS-COV) that erupted in 2012 and persisted to date, and a novel coronavirus that broke out in 2019 (2019-nCoV), all of which are β-coronaviruses.

Middle East Respiratory Syndrome (MERS) is a disease caused by Middle East Respiratory Syndrome coronavirus (MERS-CoV) infection. In June 2012, the first MERS case was found in Saudi Arabia, and a novel coronavirus was isolated from a sputum sample of the case. This virus was subsequently named MERS-CoV by the coronavirus group of the International Committee on Taxonomy of Viruses. The virus spread in the Middle East and spread to Asia, Africa, Europe and North America. According to WHO statistics, as of Oct. 6, 2015, there were 1,589 infections and 567 deaths worldwide, with a mortality rate of 35.6% In particular, the MERS epidemic imported from the Middle East to South Korea in May and June 2015 resulted in 186 infections and 36 deaths. Even one MERS case was imported into China. It brought a serious threat to the global public health system. MERS-CoV virus and SARS virus broke out in 2003 belong to (β-*Coronavirus* subgenus, but they have a higher lethality rate than SARS-CoV. MERS-CoV may spread in the form of aerosol, and thus is difficult to prevent and control. Neutralizing antibodies to MERS-CoV can be detected in the serum of dromedarycamels in many countries in the Middle East, suggesting that dromedary camel, which is an important vehicle in Middle East countries, is an intermediate host for MERS-CoV. Therefore, the sporadic MERS-CoV infection of humans in the Middle East has happened frequently since the discovery of MERS-CoV in 2012. As a result, with the increasing frequency of international communications, the risk of MERS spreading around the world has always existed. At present, there are still no vaccines and effective treatments in the world. Thus, it is urgent and important to develop a safe and effective vaccine against MERS-CoV.

In 2019, there was a case of pneumonia of unknown cause, which was identified as a coronavirus by using an electron microscope, and was temporarily named 2019 novel coronavirus (2019-nCoV), and later named SARS-CoV-2. The novel coronavirus can be transmitted from person to person through respiratory tracts and droplets, as well as through the air and digestive tracts. The source of infection is mainly patients infected with the novel coronavirus, but it is not ruled out that the asymptomatic cases are also the source of transmission. The disease may not occur immediately after infection of the virus, and the incubation period of the virus is relatively long, 1-14 days, which makes it difficult to prevent and control the disease. After entering a human body, the novel coronavirus, enters cells through angiotensin converting enzyme 2 (ACE 2) to infect the human body, causing the patient to have clinical symptoms such as fever, dry cough and muscle pain. Besides, a few of patients may have symptoms such as nasal obstruction, pharyngalgia and diarrhea and severe symptoms in some patients may rapidly progress to acute respiratory distress syndrome, septic shock, metabolic acidosis which is difficult to correct, and coagulation dysfunction, causing life danger. There is no specific drug or vaccine for the moment to prevent this virus, and only symptomatic support treatment is available.

In addition, some other coronaviruses also cause many serious animal diseases, especially posing a serious threat to agricultural livestock and pets. For instance, transmissible gastroenteritis virus (TGEV) can cause severe diarrhea in pigs with extremely high mortality, and its deletion mutant virus porcine respiratory coronavirus (PRCV) can cause severe respiratory diseases in pigs; feline infectious peritonitis virus (FIPV) can cause peritonitis and ascites aggregation in cats with high mortality; canine coronavirus (CCoV) can cause gastroenteritis symptoms in dogs to varying degrees, which spreads quickly and is difficult to control, and porcine epidemic diarrhea virus (PEDV) causes intestinal diseases such as porcine epidemic diarrhea, which is easy to spread in pigs with high mortality rate. There are also murine, bovine and other coronaviruses. These coronaviruses pose a serious threat to human and animal health. Therefore, it is of great significance to develop vaccines against coronaviruses.

The surface spike protein (S protein) is the major neutralizing antigen of a coronavirus. The receptor binding domains (RBD) of the spike proteins (S proteins) of HERS-CoV, SARS-CoV and 2019-nCoV are considered as the most important antigen target domains to induce a body to produce neutralizing antibodies. The RBDs, as vaccines, can focus the neutralizing antibodies generated by body stimulation on the receptor binding of viruses, which can improve the immunogenicity and immune efficiency of the vaccines. MERS-CoV invades a cell by RBD binding to the host cell's receptor (CD26, also known as DPP4). in addition, both SARS-CoV and 2019-nCoV were found to enter a cell via their RBD binding to the host cell. receptor hACE2.

The information disclosed herein is merely intended to provide a better understanding of the general background of the present disclosure and should not be construed as an acknowledgement or an implication in any form that the information constitutes the prior art that is already known to a person skilled in the art.

SUMMARY

Objects of the Disclosure

The present disclosure aims to provide antigens of β-coronaviruses, preparation methods and uses thereof in examples of the present disclosure, based on the conclusion that MERS RBD-dimer protein could better elicit neutralizing antibodies than RBD-monomer protein, it was tried to link two nucleotide sequences encoding the identical or substantially identical RBD-monomer protein in tandem directly or via a linker fragment and to link the two expressed identical or substantially identical RBD-monomer proteins in tandem through the N-terminal and C-terminal flexible regions, and the results showed that the method could realize good expression of a single-chain RBD-dimer. Compared with a non-single-chain RBD-dimer protein formed by simply binding two RBD-monomers through cysteines therein with disulfide bonds, the single-chain RBD-dimer protein obtained in the examples of the present disclosure would not render the content of the RBD-dimer protein unstable in the production process due to unstable formation of the disulfide bonds. That is to say, the expression of most RBD-monomers and few RBD-dimers could be avoided, so that the dimeric RBD could be stably expressed and uniform in form with a greatly improved yield. Compared with the RBD-dimer protein formed by simply binding two RBD monomers through cysteines therein with disulfide bonds, the single-chain dimer expressed in the examples of the present disclosure had equivalent immunogenicity as an antigen of a β-coronavirus, and a vaccine prepared by using the single-chain dimer as the antigen of a β-coronavirus could elicit high-titer neutralizing antibodies in mice.

SOLUTION

In order to achieve the purpose of the present disclosure, examples of the present disclosure provide the following technical solution:

An antigen of a β-coronavirus, its amino acid sequence comprises an amino acid sequence arranged in a (A-B)-(A-B) pattern or an amino acid sequence arranged in a (A-B)-C-(A-B) pattern or an amino acid sequence arranged in a (A-B)-(A-B') pattern or an amino acid sequence arranged in a (A-B)-C-(A-B') pattern, where A-B represents a partial amino acid sequence or the entire amino acid sequence of a receptor binding domain of a surface spike protein of the β-coronavirus; C represents an amino acid linker sequence; and A-B' represents an amino acid sequence obtained by substitution, deletion or addition of one or more amino acids in the amino acid sequence of A-B. A protein encoded by A-B' has the identical or substantially identical immunogenicity as a protein encoded by A-B, and the antigen of the β-coronavirus has a single-chain dimer structure. Alternatively, the partial amino acid sequence of the receptor binding domain of the surface spike protein of the β-coronavirus is at least 50%, 60%, 70%, 80%, 90%, 95%, or 99% of the entire amino acid sequence of the receptor binding domain of the surface spike protein of the β-coronavirus.

In one possible embodiment of the above-mentioned antigen of a β-coronavirus, the β-coronavirus includes severe respiratory syndrome coronavirus, Middle East respiratory syndrome coronavirus, and 2019 novel coronavirus (also known as 2019-nCoV or SARS-CoV-2).

In one possible embodiment of the above-mentioned antigen of a β-coronavirus, the amino acid linker sequence includes a (GGS)$_n$ linker sequence, where n represents the number of GGSs, which is an integer more than or equal to 1; alternatively, n is an integer selected from 1 to 10, and further, an integer selected from 1 to 5; and GGS represents amino acids G, G and S.

In one possible embodiment of the above-mentioned antigen of a β-coronavirus, when the β-coronavirus is the Middle East respiratory syndrome coronavirus, the partial or entire amino acid sequence of the receptor binding domain of the surface spike protein of the β-coronavirus is any one selected from the group consisting of the following amino acid sequences:

(1) SEQ ID NO: 1, SEQ ID NO: 2, or SEQ ID NO: 3; and (2) an amino acid sequence obtained by substitution, deletion or addition of one or more amino acids in the amino acid sequence (1), where a protein encoded by the amino acid sequence has the identical or substantially identical immunogenicity as a protein encoded by the amino acid sequence (1).

Alternatively, the partial amino acid sequence of the receptor binding domain of the surface spike protein of the β-coronavirus includes SEQ ID NO: 2.

The sequences of SEQ ID NO: 1, SEQ ID NO: 2, and SEQ ID NO: 3 are all derived from a part of the MERS-CoV S protein (GenBank: AFS88936.1 on NCBI), which are E367-Y606 region, E367-N602 region, and V381-L588 region of the RBD of the MERS-CoV S protein, respectively.

In one possible embodiment of the above-mentioned antigen of a β-coronavirus, when the β-coronavirus is the Middle East respiratory syndrome coronavirus, the amino acid sequence of the antigen of the β-coronavirus includes any one selected from the group consisting of the following amino acid sequences:

(1) two repeated amino acid sequences of SEQ ID NO: 1 linked in tandem by a GGSGGS linker sequence, namely E367-Y606-GGSGGS-E367-Y606;

(2) two repeated amino acid sequences of SEQ ID NO: 1 linked in tandem by a GGS linker sequence, namely E367-Y606-GGS- E367-Y606;

(3) two repeated amino acid sequences of SEQ ID NO: 1 linked directly in tandem, namely E367-Y606-E367-Y606.

(4) two repeated amino acid sequences of SEQ ID NO: 2 linked in tandem by a GGS linker sequence, namely E367-N602-GGS-E367-N602;

(5) two repeated amino acid sequences of SEQ ID NO: 2 linked directly in tandem by a GGS linker sequence, namely E367-N602-E367-N602;

(6) two repeated amino acid sequences of SEQ ID NO: 3 linked by a GGSGGSGGSGS linker sequence, namely V381-L588-GGSGGSGGSGGSGGSGGS-V381-L588, (7) two repeated amino acid sequences of SEQ ID NO: 3 linked in tandem by a GGSGGSGGSGS linker sequence, namely V38 -L588-GGSGGSGGSGGSGS-V38 I -L588;

(8) two repeated amino acid sequences of SEQ ID NO: 3 linked in tandem by a GGSGGSGGS linker sequence, namely V381-L588-GGSGGSGGS-V381-L588;

(9) two repeated amino acid sequences of SEQ ID NO: 3 linked in tandem by a GGS linker sequence, namely V381-L588-GGS-V381-L588; and

(10) two repeated amino acid sequence of SEQ ID NO: 3 linked directly in tandem, namely V38 -L588-V381-L588;

Alternatively, the amino acid sequence of the antigen of the β-coronavirus includes two repeated amino acid sequences of SEQ ID NO: 2 linked directly in tandem, namely E367-N602-E367-N602.

In one possible embodiment of the above-mentioned antigen of the β-coronavirus, when the β-coronavirus is the 2019 novel coronavirus, the partial or entire amino acid sequence of the receptor binding domain of the surface spike protein of the β-coronavirus is any one selected from the group consisting of the following amino acid sequences:

(1) SEQ ID NO: 5, SEQ ID NO: 6, or SEQ ID NO: 7; and
(2) an amino acid sequence obtained by substitution, deletion or addition of one or more amino acids to the amino acid sequence (1), where the protein encoded by the amino acid sequence has the identical or substantially identical immunogenicity as the protein encoded by (1).

Alternatively, the partial amino acid sequence of the receptor binding domain of the surface spike protein of the β-coronavirus includes SEQ ID NO: 6.

The sequences of SEQ ID NO: 5, SEQ ID NO: 6, and SEQ ID NO: 7 are all derived from a part of the S protein sequence of the WH01 strain of 2019-nCoV (GenBank on NCBI: QHR63250), which are R319-S530 region, R319-K537 region, and R319-F541 region of the RBD of the 2019-nCoV S protein, respectively.

In one possible embodiment of the above-mentioned antigen of a β-coronavirus, when the β-coronavirus is the 2019 novel coronavirus, the amino acid sequence of the antigen of β-coronavirus includes any one selected from the group consisting of the following amino acid sequences:

two repeated amino acid sequences of SEQ ID NO: 5 linked directly in tandem, namely R319-S530-R319-S530, two repeated amino acid sequences of SEQ ID NO: 6 linked directly in tandem, namely R319-K537-R319-K537; and two repeated amino acid sequences of SEQ I NO: 7 linked directly in tandem, namely R319-F541-R319 -F541.

Alternatively, the amino acid sequence of the antigen of the β-coronavirus includes two repeated amino acid sequences of SEQ ID NO: 6 linked directly in tandem, namely R319-K537-R319-K537.

In one possible embodiment of the above-mentioned antigen of a β-coronavirus, when the β-coronavirus is the severe respiratory syndrome coronavirus, the partial or entire amino acid sequence of the receptor binding domain of the surface spike protein of the β-coronavirus is any one selected from the group consisting of the following amino acid sequences:

(1) SEQ ID NO: 8; and
(2) an amino acid sequence obtained by substitution, deletion or addition of one or more amino acids in the amino acid sequence (1), where a protein encoded by the amino acid sequence has the identical or substantially identical immunogenicity as a protein encoded by the amino acid sequence (1).

The sequence of SEQ ID NO: 8 is derived from a part of the S protein sequence of SARS-CoV (GenBank on NCBI: AAR07630), which is R306-Q523 region of the RBD of the SARS-CoV S protein.

In one possible embodiment of the above-mentioned antigen of a β-coronavirus, when the β-coronavirus is the severe respiratory syndrome coronavirus, the amino acid sequence of the antigen of the β-coronavirus includes two repeated ammo acid sequences of SEQ m NO: 8 linked directly in tandem, namely R306-Q523-R306-Q523.

In one possible embodiment of the above-mentioned antigen of a β-coronavirus, the nucleotide sequence encoding two repeated amino acid sequences of SEQ ID NO: 1 linked in tandem by the GGSGGS linker sequence is shown as SEQ ID NO: 9;

the nucleotide sequence encoding two repeated amino acid sequence of SEQ ID NO: 1 linked in tandem by the GGS linker sequence is shown as SEQ ID NO: 10;

the nucleotide sequence encoding two repeated amino acid sequence of SEQ ID NO: 1 linked directly in tandem is shown as SEQ ID NO: 11;

the nucleotide sequence encoding two repeated amino acid sequence of SEQ ID NO: 2 linked in tandem by the GGS linker sequence is shown as SEQ ID NO: 12;

the nucleotide sequence encoding two repeated amino acid sequence of SEQ ID NO: 2 linked directly in tandem is shown as SEQ ID NO: 13;

the nucleotide sequence encoding two repeated amino acid sequence of SEQ ID NO: 3 linked in tandem by the GGSGGSGGSGGSGGS linker sequence is shown as SEQ ID NO: 14;

the nucleotide sequence encoding two repeated amino acid sequence of SEQ ID NO: 3 linked in tandem by the GGSGGSGGSGGS linker sequence is shown as SEQ ID NO: 15;

the nucleotide sequence encoding two repeated amino acid sequence of SEQ ID NO: 3 linked in tandem by the GGSGGSGGS linker sequence is shown as SEQ ID NO: 16;

the nucleotide sequence encoding two repeated amino acid sequence of SEQ ID NO: 3 linked in tandem by the GGS linker sequence is shown as SEQ ID NO: 17;

the nucleotide sequence encoding two repeated amino acid sequence of SEQ ID NO: 3 linked directly in tandem is shown as SEQ ID NO: 18;

the nucleotide sequence encoding two repeated amino acid sequence of SEQ ID NO: 5 linked directly in tandem is shown as SEQ ID NO: 19;

the nucleotide sequence encoding two repeated amino acid sequence of SEQ ID NO: 6 linked directly in tandem is shown as SEQ ID NO: 20;

the nucleotide sequence encoding two repeated amino acid sequence of SEQ ID NO: 7 linked directly in tandem is shown as SEQ ID NO: 21; and the nucleotide sequence encoding two repeated amino acid sequence of SEQ ID NO: 8 linked directly in tandem is shown as SEQ ID NO: 23.

The present disclosure also provides a method for preparing the above-mentioned antigen of a β-coronavirus, which includes the following steps: adding a sequence encoding a signal peptide to the 5'-terminal of a nucleotide sequence encoding the antigen of the β-coronavirus, adding a terminator codon to the 3'-terminal for cloning and expression, screening correct recombinants, transfecting the expression system cell for expression, collecting cell supernatants after expression, and purifying to obtain the antigen of the β-coronavirus.

In one possible embodiment of the above method, the cells of the expression system include mammalian cells, insect cells, yeast cells or bacterial cells. Alternatively, the mammalian cells include 293T cells or CHO cells, and the bacterial cells include *Escherichia coli* cells.

The present disclosure further provides a nucleotide sequence for encoding the above-mentioned antigen of a β-coronavirus, a recombinant vector including the nucleotide sequence, and an expression system cell including the recombinant vector.

The present disclosure further provides use of the above-mentioned antigen of a β-coronavirus, the nucleotide sequence encoding the antigen of the β-coronavirus, the recombinant vector including the nucleotide sequence, and the expression system cell including the recombinant vector in the preparation of a vaccine against the β-coronavirus.

The present disclosure further provides a vaccine against a β-coronavirus, which includes the above-mentioned antigen of a β-coronavirus and an adjuvant.

In one possible embodiment of the above-mentioned vaccine against a β-coronavirus, the adjuvant is selected from an aluminum adjuvant, an MF59 adjuvant or an MF59-like adjuvant. The present disclosure further provides a DNA vaccine against a β-coronavirus, which includes a recombinant vector including a DNA sequence encoding the above-mentioned antigen of a β-coronavirus.

The present disclosure further provides an mRNA vaccine against a β-coronavirus, which includes a recombinant vector including an mRNA sequence encoding the above-mentioned antigen of a β-coronavirus.

The present disclosure further provides a viral vector vaccine against a β-coronavirus, which includes a recombinant viral vector including a nucleotide sequence encoding the above-mentioned antigen of a β-coronavirus. Alternatively, the viral vector is one or more selected from the group consisting of an adenovirus vector, a poxvirus vector, an influenza virus vector and an adeno-associated virus vector.

Beneficial Effects (1) In the antigen of a β-coronavirus of an example of the present disclosure, based on the conclusion that MERS RBD-dimer protein could better elicit neutralizing antibodies than RBD-monomer protein, it was found that the MFRS RBD-dimer protein could form an end-to-end dimer by further analyzing the crystal structure of the MERS-CoV RBD-dimer protein. Therefore, the inventor tried to link two nucleotide sequences encoding the identical or substantially identical RBD-monomer proteins directly in tandem or via a linker fragment and to link two obtained identical or substantially identical RBD-monomer proteins in tandem through flexible regions at the N-terminal and C-terminal, and the results showed that the method could realize good expression of a single-chain dimer. Compared with a non-single-chain RBD-dimer protein formed by simply binding two RBD monomers through cysteines therein with disulfide bonds, the single-chain RBD-dimer protein obtained in the example of the present disclosure would not render the content of the RBD-dimer protein unstable in the production process due to unstable formation of the disulfide bonds. That is to say, the expression of most RBD-monomers and few RBD-dimers could be avoided, so that the RBD-dimer could be stably expressed and uniform in form with a greatly improved yield. Compared with the non-single-chain RBD-dimer protein formed by simply binding two RBD monomers through cysteines therein with disulfide bonds, the single-chain dimer expressed in the example of the present disclosure had equivalent immunogenicity as an antigen of a β-coronavirus, and a vaccine prepared by using the single-chain dimer as the antigen of a β-coronavirus could elicit high-titer neutralizing antibodies in mice.

(2) In the antigen of a β-coronavirus of an example of the present disclosure, based on the selection of amino acids in different regions of the contained RBD, the construct with the best expression was found from the first amino acid of START shown in FIG. 14A to the amino acid before the last cysteine of STOP shown in FIG. 14B, so that the influence of unpaired cysteines at the ends on the expression and the stability of the protein could be avoided to the greatest extent.

(3) In the antigen of a β-coronavirus of an example of the present disclosure, based on the selection of direct tandem connection or linker fragment-involved tandem connection of two nucleotide sequences encoding the identical or substantially identical RBD-monomer proteins, the highest expression level was found under the condition that no any exogenous linker sequence was introduced, i.e., two nucleotide sequences encoding the identical or substantially identical RBD-monomer proteins were linked directly in tandem, and the expression was also the safest because no exogenous sequence was added. Since various single-chain RBD-dimers obtained in the examples of the present disclosure had good immune effect as antigens of β-coronaviruses, the yield thereof would be crucial.

(4) In the antigen of a β-coronavirus of an example of the present disclosure, the involved end-to-end single-chain dirtier structure is suitable for severe respiratory syndrome coronavirus, Middle East respiratory syndrome coronavirus and 2019 novel coronavirus.

BRIEF DESCRIPTION OF THE DRAWINGS

FIG. 7 shows the pathological results of the examination of the protective efficacy of the vaccine on the lung tissue of mice in Example 8 in which the lungs from the challenged mice in Example 7 after necroscopy were fixed in 4% paraformaldehyde, embedded in paraffin, stained with hematoxylin and eosin and sliced to obtain tissue sections for observation of pathological changes, where AddaVax indicates the use of AddaVax adjuvant; Alum indicates the use of aluminum adjuvant; and 3 µg, 10 µg, and 30 µg indicate the amounts of the immunogen used per immunization. Slight, Mild and Severe indicate different grades of lung tissue lesions, respectively.

FIG. 8 shows the structure of MERS-CoV-RBD dimer (E367-Y606) analyzed in Example 9.

MERS-CoV (AFS88936), SARS-CoV (AAS00003), SARS-CoV-2 (QHR63290), Bat-CoV_HKU5 (ABN10875), Rousettus_bat-CoV (AOG30822), Bat-CoV_BM48-31 (ADK66841), Bat-CoV_HKU9 (ABN10911), Bat_Hp-beta-CoV (AIL94216), SARS-related-CoV (APO40579), BtRs-Beta-CoV (QDF43825), Bat-SARS-like-CoV (ATO98231), SARS-like-CoV_WIV16 (ALK02457), Bat-CoV (ARI44804), BtR1-Beta-CoV (QDF43815), HCoV_HKU1 (AZS52618), MCoV_MHV1 (ACN89742), Beta-CoV_HKU24 (AJA91217), HCoV_OC43 (AAR01015), and BetaCoV_Erinaceus (AGX27810).

Figure 15:
Figure 15:
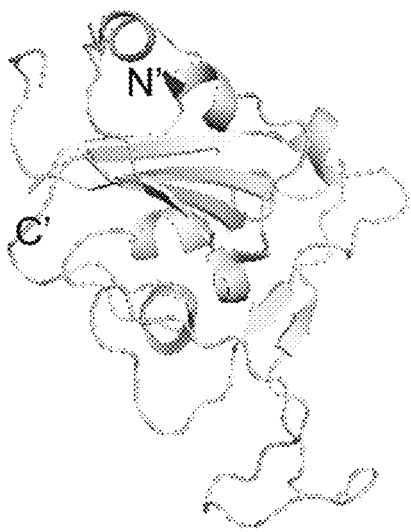

FIG. 15 is a mimic diagram showing the structure of SARS-CoV-RBD dimer or 2019-nCoV-RBD dimer in example 13 and the construct of the expression 2019-nCoV-RBD dimer, the 2019-nCoV-RBD monomer and the SARS-CoV-RBD dimer designed.

Figure 16:
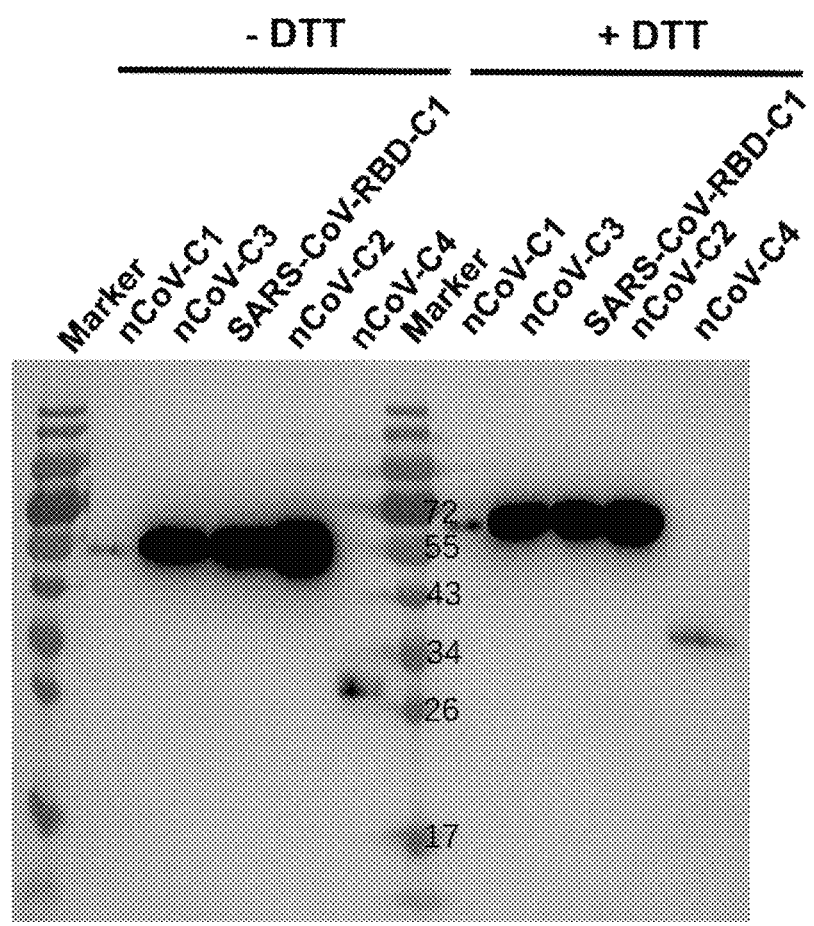

FIG. 16 shows the results of Western blot under reduced conditions (+DTT) or non-reduced conditions (-DTT) for several single-chain dimers of SARS-CoV-RBD and 2019-nCoV- RBD expressed in Example 13.

Figure 17:
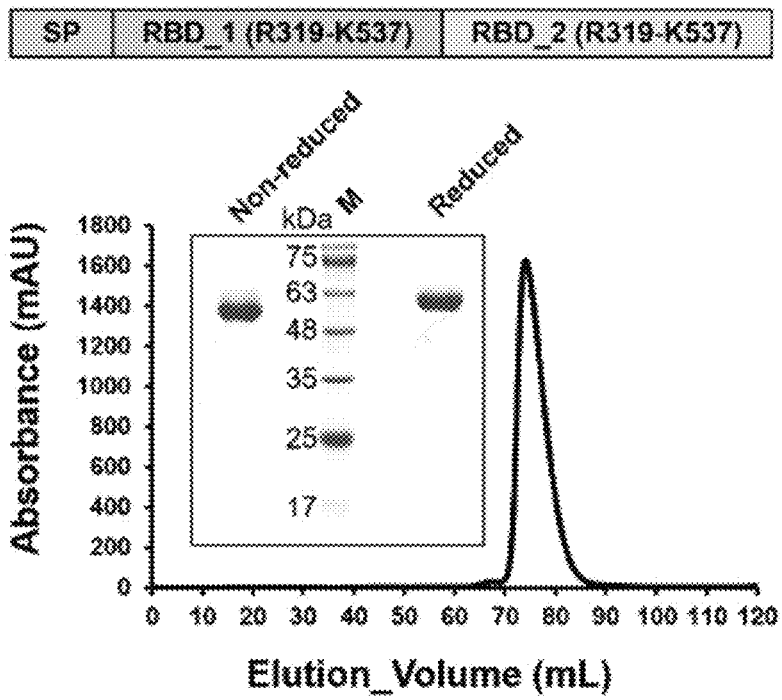

FIG. 17 shows the ultraviolet absorbance at 280 nm for 2019-nCoV-RBD-C2 antigen purified in Example 14, and the results of SDS-PAGE of the purified single-chain dirtier under reduced conditions (+DTT) or non-reduced conditions (-DTT).

Figure 18:
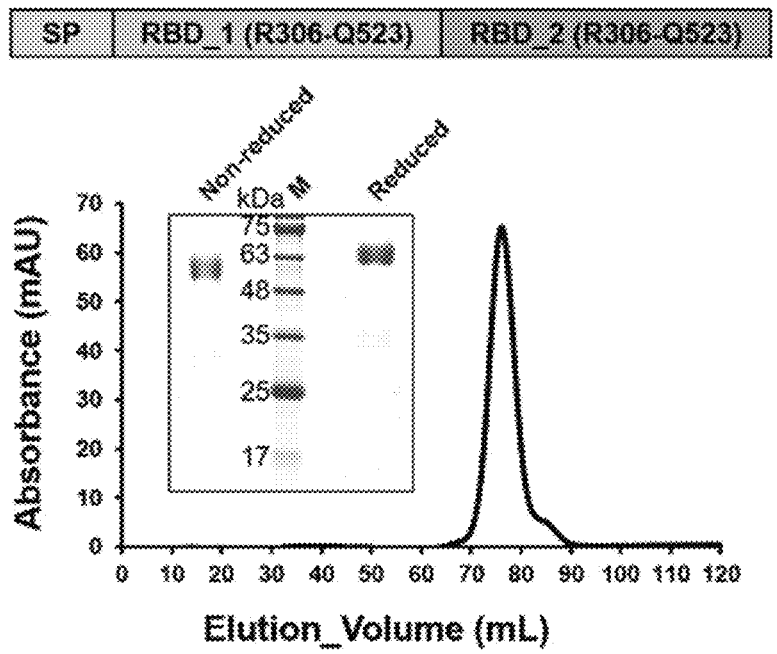

FIG. 18 shows the ultraviolet absorbance at 280 nm for SARS-CoV-RBD-C1 antigen purified in Example 14, and the results of SDS-PAGE of the purified single-chain dimer under reduced conditions (+DTT) or non-reduced conditions (-DTT).

Figure 19:
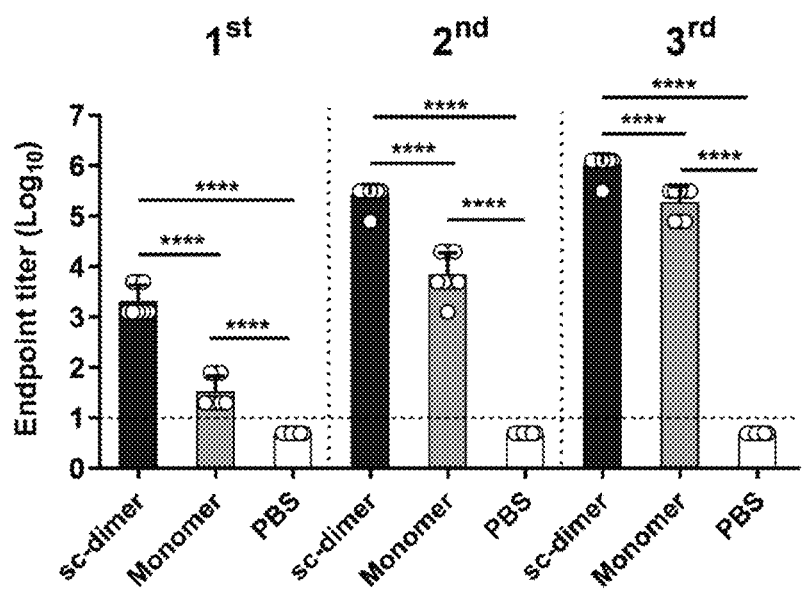

FIG. 19 shows the titers of 2019-nCoV-RBD specific IgG antibody in sera collected from mice after three immunizations (19 days after the first immunization, 14 days after the second immunization, and 14 days after the third immunization) in Example 15, respectively, where sc-dimer indicates that single-chain nCoV-RBD dimer was used as the immunogen, and Monomer indicates that nCoV-RBD-monomer was used as the immunogen. Significant difference analysis: ****, P<0.0001.

Figure 20:
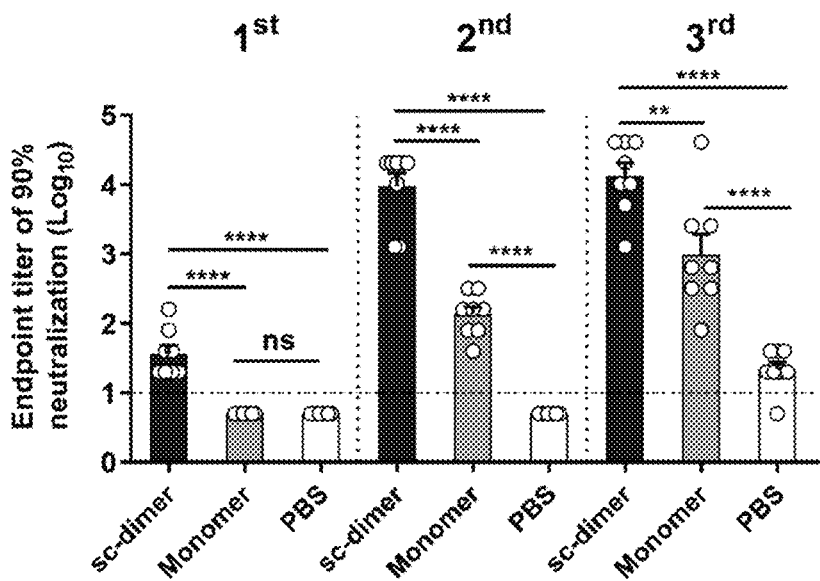

FIG. 20 shows the 90% neutralization titers of antibodies against 2019-nCoV pseudovirus in sera collected from mice after three immunizations (19 days after the first immunization, 14 days after the second immunization, and 14 days after the third immunization) in Example 15, where sc-dimer indicates that single-chain nCoV-RBD dimer was used as the immunogen, and Monomer indicates that nCoV-RBD-monomer was used as the immunogen. Significant difference analysis: ns, P=0.05; , P<0.01; **, P<0.0001.

FIG. 21 shows the 50% neutralization titers of antibodies against 2019-nCoV euvirus (2020XN4276 strain) in sera collected after the second immunization (14 days after the second immunization) of mice in Example 15, where sc-dimer indicates that single-chain nCoV-RBD dimer was used as the immunogen, and Monomer indicates that nCoV-RBD-monomer was used as the immunogen.

FIG. 22 shows the titers of SARS-RBD-specific IgG antibody in sera collected after three immunizations of mice in Example 16 (19 days after the first immunization, 14 days after the second immunization, and 14 days after the third immunization), where sc-dimer indicates that single-chain SARS-CoV-RBD dimer was used as the immunogen, and Monomer indicates that SARS-CoV-RBD-monomer was used as the immunogen. Significant difference analysis: ns, P>0.05; *, P<0.05; , P<0.01; **, P<0.0001.

Figure 23:
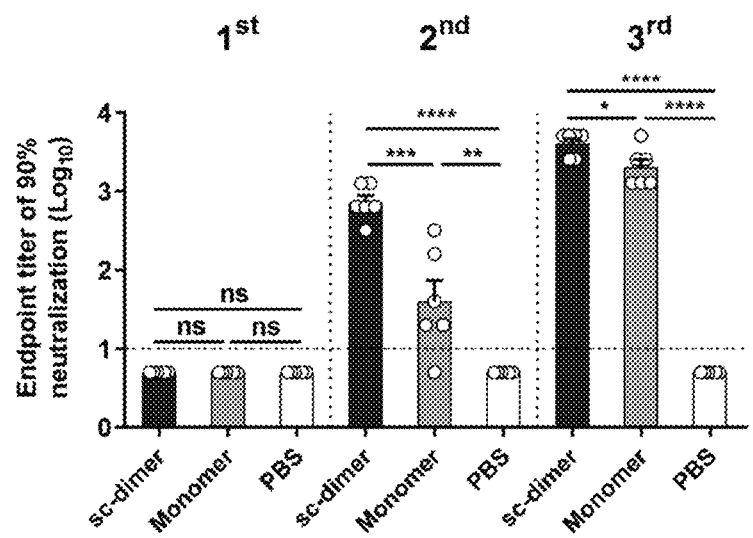

FIG. 23 shows the 90% neutralization titers of antibodies against SARS-CoV pseudovirus in sera collected from mice after three immunizations (19 days after the first immunization, 14 days after the second immunization, and 14 days after the third immunization) in Example 16, where sc-dimer indicates that single-chain SARS-CoV-RBD dimer was used as the immunogen, and Monomer indicates that SARS-RBD-monomer was used as the immunogen. Significant difference analysis: ns, $P>0.05$; *, $P<0.05$; , $P<0.01$; *, $p<0.001$; ****, $P<0.0001$.

DETAILED DESCRIPTION OF THE PRESENT DISCLOSURE

In order to make the objects, technical solutions and advantages of the examples of the present disclosure clearer, the technical solutions in the examples of the present disclosure will be clearly and completely described below. Apparently, the described examples are some, but not all examples of the present disclosure. All other examples derived from the examples of the present disclosure by a person skilled in the art without creative work shall fall within the scope of protection of the present disclosure.

Furthermore, in the following detailed description, numerous specific details are set forth in order to provide a better understanding of the present disclosure. It will be understood by those skilled in the art that the present disclosure may be practiced without some of these specific details. In some examples, materials, elements, methods, procedures, and the like that are well known to those of skill in the art have not been described in detail so as not to obscure the present disclosure.

Throughout the specification and claims, unless expressly indicated otherwise, the terms "comprise" or "include", or variations such as "comprises" or "comprising", "includes" or "including" will be understood to imply the inclusion of a stated element or component but not the exclusion of any other element or component.

Explanation of Terms

Disulfide-linked non-single-chain RBD dimer and RBD monomer refer to those obtained by inserting a nucleotide sequence encoding RBD monomer into a vector, then transfecting cells of an expression system for expression, collecting cell supernatants after expression, and purifying, where two RBD monomers in a disulfide-linked non-single-chain RBD dimer are simply disulfide-bonded through cysteines therein. As used herein, disulfide-linked non-single-chain RBD dimer and non-single-chain RBD-dimer protein have the same meaning; and RBD monomer, monomeric RBD, and RBD-monomer protein all have the same meaning.

Single-chain RBD dimer is a recombinant protein obtained by linking two nucleotide sequences encoding identical or substantially identical RBD monomers in tandem directly or via a linker fragment, adding a sequence encoding a signal peptide to the 5'-terminal of the nucleotide sequence and a terminator codon to the 3'-terminal of the nucleotide sequence for cloning and expression, screening correct recombinants, transfecting cells of an expression system cell for expression, collecting cell supernatants after expression, and purifying, where the protein contains two RBD monomers which are identical or substantially identical and can be directly linked together with peptide bonds or linked together through a linker sequence (such as GGS, GGSGGS and the like). As used herein, single-chain RBD-dimer, single-chain RBD dimer, single-chain dimer, sc-RBD dimer, single-chain RBD dimer and the like all have the same meaning.

EXAMPLE 1

Preparation of Recombinant Baculovirus Expressing MERS-CoV Antigen, and Expression and Purification of RBD Protein A nucleotide sequence (shown as SEQ ID NO: 24) encoding an amino acid RBD (E367-Y606) sequence (shown as SEQ ID NO: 1) in MERS-CoV S protein (having a sequence shown as GenBank: AFS88936.1) was cloned between EcoR I and Xho I restriction enzyme cutting sites of a pFastBac vector (pFastBac-SP, available from Invitrogen) containing gp67 signal peptide after the addition of a translation termination codon to the 3'-terminal thereof, so that the protein encoding region was subjected to fusion expression behind the signal peptide gp67 sequence for secretion of the protein of interest having 6 histidines at the C-terminal thereof, thereby obtaining a vector pFastBac-SP-MFRS-RBD (E367-Y606). The vector was then transfected into the cells of the expression system for expression, and after expression, cell supernatants were collected and purified.

Figure 1:
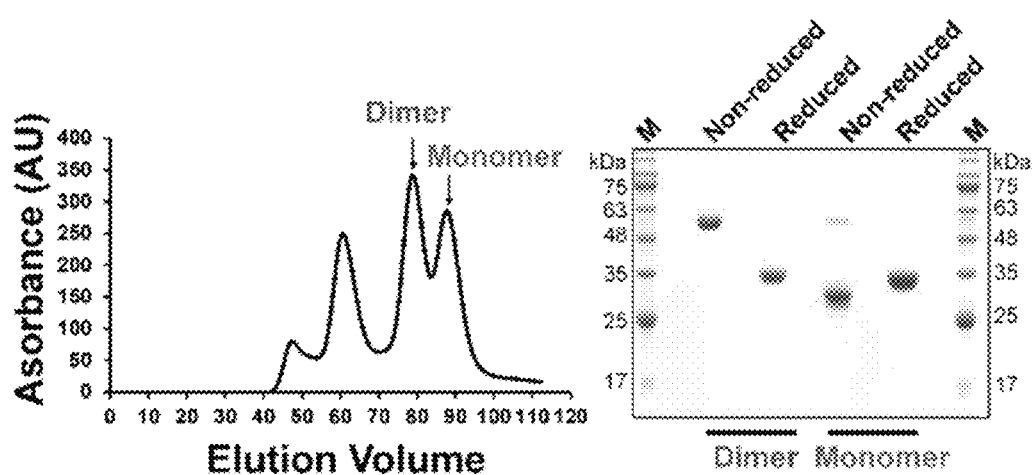
FIG. 1 shows an ultraviolet absorption profile for the RBD protein obtained by means of a constructed vector pFastBac-SP-MERS-RBD (E367-Y606) in Example 1 subjected to molecular sieve chromatography using a Superdex 200 Hiload 16/60 column (GE), and an electrophoretogram for the protein subjected to SDS-PAGE under reduced conditions (+DTT) or non-reduced conditions (−DTT) obtained by collecting Dimer peaks and Monomer peaks in the ultraviolet absorption profile.

The obtained RBD protein was purified through molecular sieve chromatography using a Superdex 200 Hiload 16/60 column (GE), and a typical ultraviolet absorption profile for protein purification is shown in FIG. 1. There was one dimer peak and one monomer peak, SDS-PAGE was conducted on the elution peak of MERS-RBD protein in the vicinity of the elution volume of 78 mL. Under non-reduced conditions (without DTT), the size of the protein in the vicinity of the elution volume of 78 mL was approximately 60 Kd; whereas under reduced conditions (with DTT added), the size was approximately 30 Kd, which confirmed that the protein obtained in this peak was a dimer. SDS-PAGE was conducted on the elution peak in the vicinity of 90 mL of the elution volume, the size of the protein of interest was approximately 30 Kd under non-reduced conditions (without DTT) and reduced conditions, which confirmed that the peak was mainly RBD monomer. The dimer or monomer used in each of Examples 2 to 9 below was the disulfide-linked non-single-chain RBD dirtier or RBD monomer obtained in this Example.

EXAMPLE 2

Experiment for Immunization of Mice with MERS-RBD Protein

MF59 (AddaVax used below was an MF59-like adjuvant) and aluminum adjuvant two commonly used adjuvants approved by SFDA, were used as vaccine components to provide more direct guidance for subsequent clinical trials. An in vitro neutralization experiment, as a classic method, was conducted to detect the protective efficacy of vaccines. Therefore, different doses of antigen were mixed with AddaVax adjuvant and Imject™ Alum adjuvant separately for immunization. The immunization groups, the types of RBD used in each group, the amount of RBD used in each immunization and the adjuvants are shown in Table 1 in which the blank space indicates "None".

MERS-RBD antigen (dimer or monomer) obtained in Example 1 was diluted with normal saline to a desired concentration and emulsified with adjuvants in groups.

BALB/c mice aged 4-6 weeks (average weight 15-20 g, similarly hereinafter) were immunized in groups, with 6 mice in each group.

TABLE 1

| Group | Immunogen | Forms | Dose | Adjuvant |
|---|---|---|---|---|
| 1 | RBD | Dimer | 3 μg | Alum |
| 2 | RBD | Dimer | 10 μg | Alum |
| 3 | RBD | Dimer | 30 μg | Alum |
| 4 | RBD | Dimer | 3 μg | AddaVax |
| 5 | RBD | Dimer | 10 μg | AddaVax |
| 6 | RBD | Dimer | 30 μg | AddaVax |
| 7 | RBD | Monomer | 3 μg | Alum |
| 8 | RBD | Monomer | 10 μg | Alum |
| 9 | RBD | Monomer | 30 μg | Alum |
| 10 | RBD | Monomer | 3 μg | AddaVax |
| 11 | RBD | Monomer | 10 μg | AddaVax |
| 12 | RBD | Monomer | 30 μg | AddaVax |
| 13 | PBS | — | | |
| 14 | PBS | — | | Alum |
| 15 | PBS | — | | Addavax |

Figure 2:
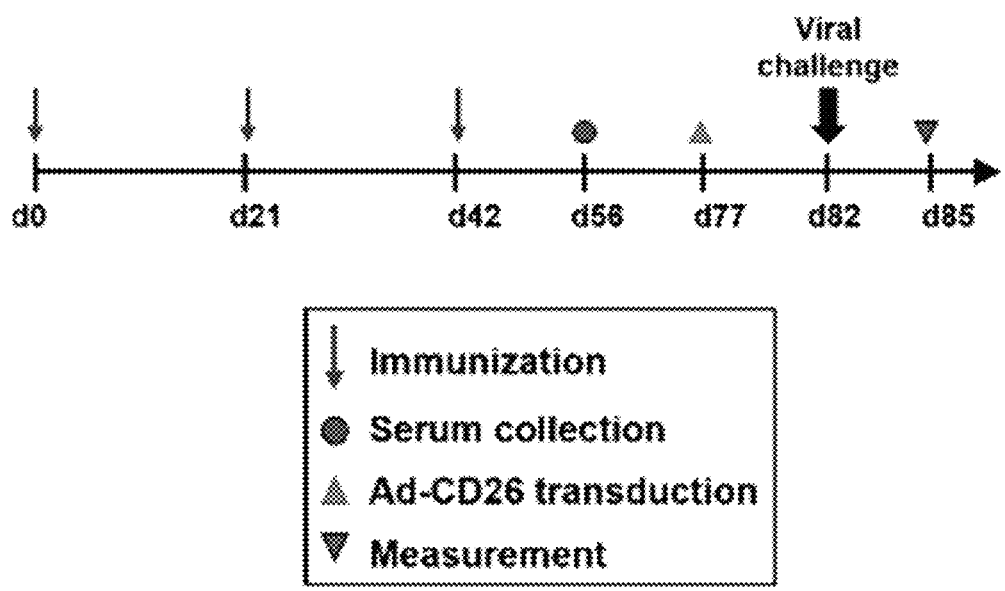
FIG. 2 is a schematic diagram of the immunization and MERS-CoV challenge strategies in Examples 2 to 7.

The immunization was conducted according to a strategy as shown in FIG. 2. i.e., by means of intramuscular injection into the thigh, each mouse received three immunizations with vaccine at day 0, day 21 and day 42, respectively, each time in a vaccination volume of 100 μl. On the day 56 (namely, the 14th day after the third immunization), blood was collected from the tails of mice. Mouse sera were obtained by centrifugation at 3000 rpm for 10 minutes after standing, and stored at −20° C. in a refrigerator for specific antibody titer assay and pseudovirus neutralization assay.

EXAMPLE 3

ELISA Assay of Vaccine-Elicited Specific Antibody Titer (1) The RBD-monomer protein of MERS-CoV was diluted to 3 μg/ml with an ELISA coating solution (Solarbio, C1050), and 100 μl of the resulting solution was added to each well of a 96-well ELISA plate (Coring, 3590) and placed at 4° C. for 12 hours.

(2) The coating solution was removed, and then PBS was added to wash once. 5% skim milk prepared with PBS was added to a 96-well plate in an amount of 100 μper well as a blocking solution for blocking and placed at room temperature for 1 hour. After the completion of blocking, the plate was washed once with PBS solution.

(3) Mouse serum was diluted during blocking. Serum samples were also diluted with the blocking solution. Serum samples were diluted from 20-fold. Then 100 μl of serum was added to each well of the ELISA plate, while the blocking solution was added for the negative control, incubated at 37° C., for 2 hours, and then washed with PBST for 4 times.

(4) Goat anti-mouse IgG-ITIRP antibody (Abcam, ab6789) diluted 1:2000 with the blocking solution was added and incubated at 37° C. for 1.5 hours, and then washed with PBST for 5-6 times. Plates were developed with TMB substrate, which was followed by stopping the reactions with 2 M hydrochloric acid for a proper time, and the absorbance was measured at 450 nm using a microplate reader. Antibody titer values were defined as the highest dilution of serum with a response value greater than 2.5 times the negative control value. The titer of a sample was defined as half of the lowest dilution (limit of detection) at which the response value was still less than 2.5-fold background value, namely, 1: 10.

Figure 3:
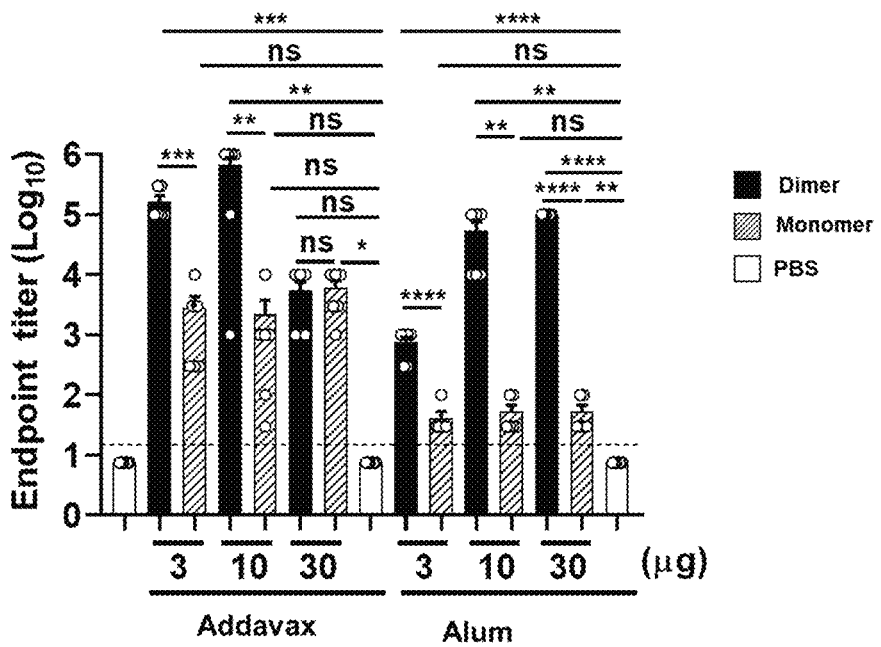
FIG. 3 shows the results of Example 3, i.e., the titers of MERS-CoV RBD specific IgG antibody in sera collected from mice according to the immunization strategy in FIG. 2 after the third immunization in Example 2, where Dimer indicates that MERS-CoV RBD-dimer was used as the immunogen; RBD-monomer indicates MERS-CoV RBD-monomer was used as the immunogen; AddaVax indicates the use of AddaVax adjuvant; Alum indicates the use of aluminum adjuvant; no indication of adjuvant means no use of adjuvant; and 3 μg, 10 μg, and 30 μg, indicate the amounts of the immunogen used per immunization. Significant difference analysis: ns, $P>0.05$; *, $P<0.05$; , $P<0.01$; *, $p<0.001$; ****, $P<0.0001$.

As shown in FIG. 3, significantly different levels of antibodies were elicited for the RBD dimer group and monomer group at doses of 3 μg and 10 μg with the AddaVax adjuvant, and significantly different levels of antibodies were elicited for the two groups at doses of 3 μg, 10 μg and 30 μg with the aluminum adjuvant, and the dimer group elicited higher levels of antibodies, indicating that the dimeric RBD antigen had a significantly higher ability to activate the antibody response in mice than the RBD monomer vaccine.

The RBD-monomer protein of MERS-CoV was used as the coating protein in all ELISA assays in the examples of the present disclosure,

EXAMPLE 4

Preparation of MERS-CoV Pseudovirus

PNI43-Lucii Pseudovirus Packaging (1) Cell plating: on the day before transfection, 293T cells grown in logarithmic phase were harvested by trypsinization, counted, reseeded and cultured overnight in a 10 cm petri dish, and transfected (without antibiotics) when the confluence of the cells reached 70-90% over 18-24 hours.

(2) Plasmid co-transfection by a PEI method: a total of 20 82 g of plasmid (10 μg of HIV pNL4-3.Luc.RE (Invitrogen) and 10 μg of pCAGGS-MERS-S which was obtained by inserting a DNA sequence encoding MERS Spike protein (M1-H1352) into EcoRI and XhoI sites of pCAGGS vector) and 40 μL of PEI (2 mg/ml) were dissolved in normal saline or HBS separately, to a final volume of 500 μL, and mixed evenly. After standing for 5 minutes, the two solutions were mixed, followed by standing for 20 minutes. The mixture was then added dropwise to the cell culture dish, and 4-6 hours later, the cells were washed twice with PBS and provided with a fresh serum-free medium.

(3) Virus harvesting: after transfection for 48 hours, cells and supernatants were harvested, centrifuged slow at 1000 rpm for 10 minutes to remove cell debris, packed, and single use aliquots were stored at −80° C. to avoid the decrease of virus titers caused by repeated freezing and thawing.

(4) Infection: on the first day, the cells were seeded and cultured overnight, and the cells reached 80-100% over 18-24 hours;

On the next day, the susceptible cells were washed with PBS to remove serum and infected with the collected viral supernatant, and the culture medium was changed to a serum-containing medium 4-6 hours later. According to the experimental requirements, Luciferase values could be measured at different time points, with reference to the Luciferase Assay System Protocol or the Dual Luciferase Reporter Assay System Protocol of Promega Company. The harvested virus solution was diluted 5-fold and added to Huh7 cells (human hepatoma cells) in a 96-well plate. After 4 hours of infection, the virus solution was discarded, and the cells were washed twice with PBS, and provided with DMEM complete medium containing 10% serum. The medium was discarded 48 hours later, and the cells were washed twice with PBS and added with a cell lysis solution. After freezing and thawing once at −80° C., 20 μl of cell culture from each well was assayed for luciferase activity using a GloMax 96

Microplate Luminometer (Promega). $TCID_{50}$) was calculated by Reed-Muech method.

EXAMPLE 5

Pseudovirus Neutralization Assay of Immune Serum

The serum obtained in Example 2 was diluted in multiple ratios, mixed with 100 $TCIDD_{50}$ pseudovirus, and incubated for 30 minutes at 37° C. The mixture was then added to a 96-well plate completely covered with Huh7 cells. After incubation at 37° C. for 4 hours, the virus solution was discarded, and the cells were washed twice with PBS, and provided with a complete medium DMEM containing 10% serum. After 48 hours, the culture medium was discarded, and the cells were washed twice with PBS and added with a cell lysis solution to assay the luciferase activity. Pseudovirus having spike protein on the surface infected cells to release DNA and express rather than replicate luciferase. If the pseudovirus could not infect the cells in the presence of neutralizing antibodies, the luciferase was not expressed. The neutralization titers of the serum were examined in this way.

Figure 4:
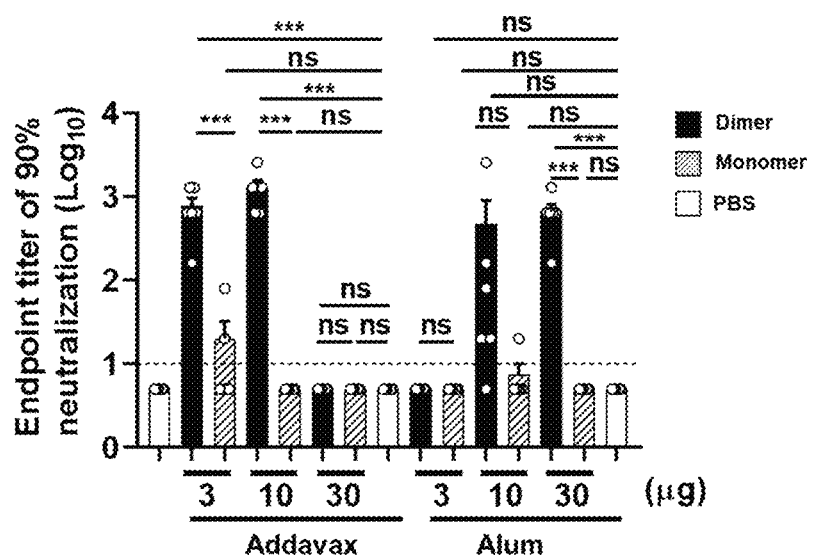
FIG. 4 shows the results of Example 5, i.e., 90% neutralization titers antibodies against MERS-CoV pseudovirus in sera collected from mice according to the immunization strategy in FIG. 2 after the third immunization in Example 2, where Dimer indicates that MERS-CoV RBD dimer was used as the immunogen; RBD monomer indicates that MERS-CoV RBD monomer was used as the immunogen; AddaVax indicates the use of AddaVax adjuvant; Alum indicates the use of aluminum adjuvant; no indication of adjuvant means no use of adjuvant; and 3 μg, 10 μg, and 30 μg indicate the amounts of the immunogen used per immunization. Significant difference analysis: ns, $P>0.05$; ***, $p<0.001$.

The results of immunogenicity assays after the third immunization are shown in FIG. 4. The result shown that the RBD dimer (E367-Y606) elicited neutralizing antibodies after three immunizations, regardless of the adavax adjuvant group or the aluminum adjuvant group (indicated by +Alum). Particularly, the mean value of the neutralizing antibodies $NT_{90}$ in the AddaVax adjuvant 10 μg group could reach more than 1:1000 (as shown in FIG. 4); whereas the RBD-monomer (E379-E589) did not elicit neutralizing antibodies after three immunizations except low neutralizing antibody production in 2 mice (as shown in FIG. 4). Pseudovirus neutralization assay demonstrated that the neutralizing antibodies induced by the RBD-dimer was much higher than that induced by the monomeric RBD.

The RBD monomer (E379-E589) was obtained by the following method: a nucleic acid fragment (shown as SEQ ID NO: 25) encoding the amino acid (E379-E589) sequence (shown as SEQ ID NO: 4) in MERS-CoV S protein was inserted into EcoRI and XhoI restriction enzyme cutting sites of pFastBac-SP to allow fusion expression of the protein coding region behind the signal peptide gp67 sequence for secretion of the protein of interest having 6 histidines at the C-terminal thereof, thereby obtaining a vector pEastBac-SP-MERS-RBD (E379-E589).

EXAMPLE 6

Euvirus Neutralization of Immune Serum (EMC Strain)

Figure 5:
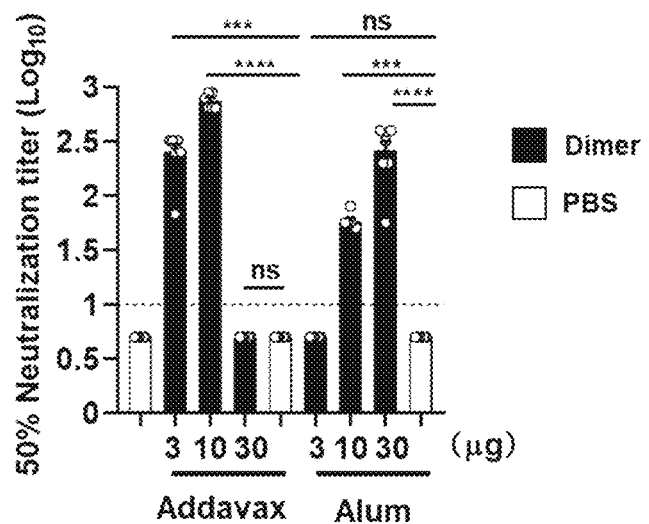
FIG. 5 shows the results of Example 6, i.e., 50% neutralization titers of antibodies against MERS-CoV euvirus (EMC strain) in sera collected from mice according to the immunization strategy in FIG. 2 after the third immunization in Example 2, where Dimer indicates that MERS-CoV RBD dimer was used as the immunogen; AddaVax indicates the use of Addavax adjuvant; Alum indicates the use of aluminum adjuvant; no indication of adjuvant means no use of adjuvant; and 3 µg, 10 µg, and 30 µg indicate the amounts of the immunogen used per Significant difference analysis: ns, P>0.05; *, p<0.001; **, P<0.0001.

Neutralization assay was conducted with serum after three immunizations for MERS-CoV euvirus (EMC strain, disclosed in Yao Y, Bao W, et al. An animal model of MERS produced by infection of rhesus macaques with NIERS coronavirus. J Infect Dis. 2014,209(2):236-242. doi: 10.1093/infdis/jit590, supplied by the institute of laboratory animals of Peking Union Medical College). The results are shown in FIG. 5. The results showed that both AddaVax adjuvant and aluminum adjuvant could elicit high neutralizing antibodies in mice. The highest group (Addavax adjuvant 10 μg and RBD dimer) achieved an IC50 greater than 1:600. This result demonstrated that the dimeric RBD could elicit a higher level of neutralizing antibodies in mice by MERS-CoV euvirus neutralization assay.

EXAMPLE 7

Challenge Protection Experiment

Figure 6:
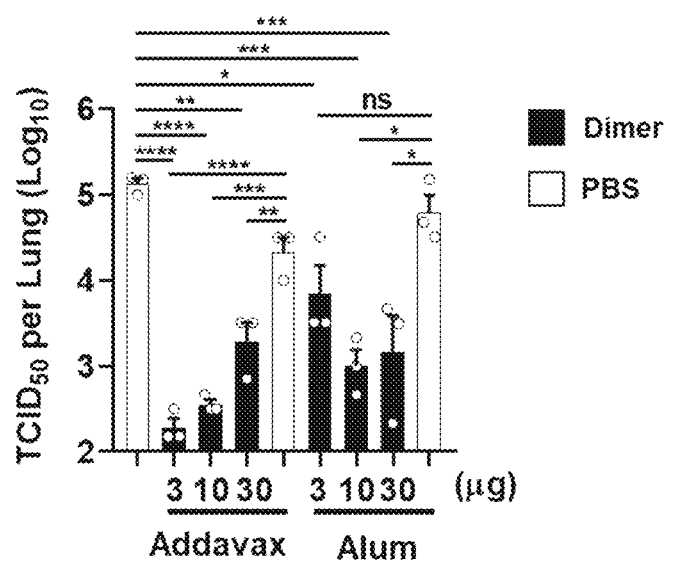
FIG. 6 shows the results of Example 7 in which mice after the third immunization were subjected to intranasal infection with adenovirus expressing hCD26 (hDPP4) according to the immunization strategy in FIG. 2, and were challenged with MERS-COV 5 days later, followed by the detection of viral titers ($TCID_{50}$) on the tissue homogenates prepared from the lungs of the mice removed 3 days later, Dimer indicates that MERS-CoV RBD dimer was used as the immunogen; AddaVax indicates the use of AddaVax adjuvant; Alum indicates the use of aluminum adjuvant; no indication of adjuvant means no use of adjuvant; and 3 µg, 10 µg, and 30 µg indicate the amounts of the immunogen used per immunization. Significant difference analysis: ns, P>0.05; *, P<0.05; , P<0.01; *, p<0.001; ****, P<0.0001.

Mice immunized three times in Example 2 were intranasally infected with adenovirus expressing hCD26 (hDPP4) on day 77, as shown in FIG. 2. This allowed transient expression of MERS-CoV receptor hCD26 in lung, making mice susceptible to MERS-CoV (see Chi H et al. DNA vaccine encoding Middle East responsive syndrome coronavirus S1 protein induces protective immune responses in mice [J]. Vaccine, 2017, 35 (16): 2069-2075). Five days later, experiments with MERS-CoV (EMC strain) challenge were conducted with a challenge dose of $5\times10^5$ pfu. Three days later after challenge, the lungs of mice were harvested, and tissue homogenate prepared therefrom was used to detect virus titers ($TCID_{50}$). The results are shown in FIG. 6. Compared with PBS control group, the viral load in lung tissue of mice in vaccine group decreased significantly. The viral load in the group with AddaVax adjuvant 3 μg and RBD dimer decreased by nearly 1000 times compared with that of the PBS group, showing a good protective efficacy. These results showed that the RBD dimer, as a vaccine, had a markedly significant protective efficacy against MERS-Co V challenge.

EXAMPLE 8

Validation of Vaccine Protection for The Lung Tissue of Mice

Figures 7, 8:
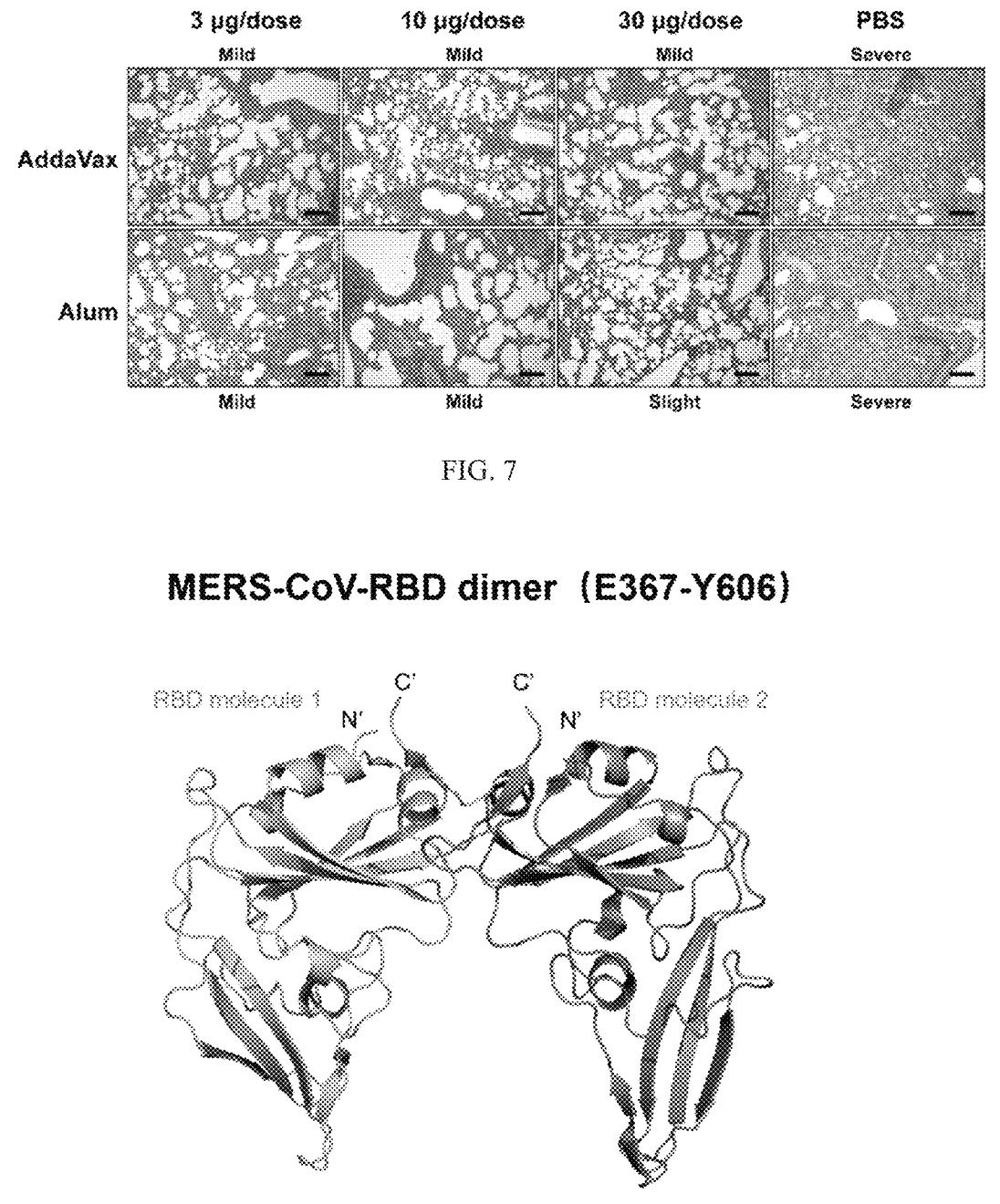

The lung tissue of mice in the MERS-CoV challenge experiment in Example 7 was fixed in 4% paraformaldehyde, and then stained with hematoxylin and eosin, and tissue sections were used to observe the pathological changes of the lung, with results as shown in FIG. 7. Lung tissues of all control mice (namely, PBS group) exhibited severe interstitial pneumonia, pulmonary alveolitis, diffuse inflammatory cell infiltration, and necrosis of bronchial epithelial cells (as shown in FIG. 7). However, milder lesions were observed in the group of mice immunized with the RBD-dimer and the pulmonary alveolus was highly visible with lower infiltration of inflammatory cells because both AddaVax and Alum adjuvants could greatly alleviate the lung injury caused by virus challenge. The small histopathological changes in the lung likely resulted from a direct inoculation of high amount ($5\times10^5$ pfu) of virus intranasally. Therefore, the RBD-dimer could substantially reduce the lung injury caused by MERS-CoV infection.

EXAMPLE 9

Crystallization and Structure Determination of MERS-RBD-Dimer

The RBD (E367-Y606) protein was expressed according to the method of Example 1, After purification, the dimer protein peaks were collected. The protein was concentrated to 10 mg/ml and mixed with the reservoir solution in a volume ratio of 1:1, and then protein crystal screening was carried out by mosquito® Protein Crystallization Screening Liquid Workstation (TTP LabTech). Diffraction-quality crystals of MERS-CoV RBD-dimer were obtained at 18° C. The crystals were collected at the Shanghai Synchrotron Radiation Facility (SSRF), and finally 2.8 Å diffraction data were obtained. The data were processed with HKL2000 software, and the structure was solved by the molecular replacement module, with the structure of MERS-CoV RBD (PDB: 4KQZ) as the search models. The results are shown in FIG. 8.

EXAMPLE 10

Structure Design of a Single-Chain RBD Dimer (Sc-RBD Dinner) Based on MERS-RBD Dinner Based on the MERS-RBD crystal structure of FIG. 8, the N-terminal (N') and C-terminal (C') of the two subunits of RBD were arranged in an end-to-end form. The N-terminal and the C-terminal each had an invisible flexible sequence (as shown in FIG. 9A), which inspired us to link two subunits as a tandem repeat single chain, namely, single-chain RBD dimer (sc-RBD) dimer).

Figure 9A:
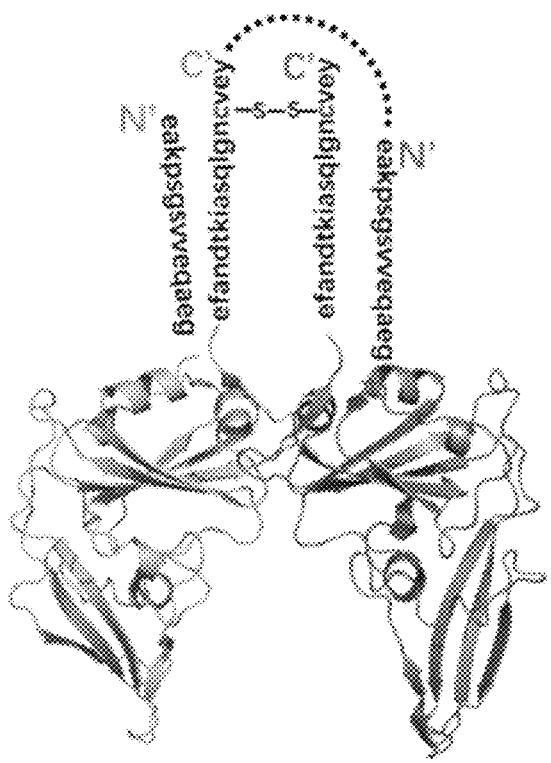
FIGS. 9A, 9B, and 9C show single-chain RBD dimers designed based on the MERS-CoV RBD-dimer structure in Example 10.
Figure 9A:
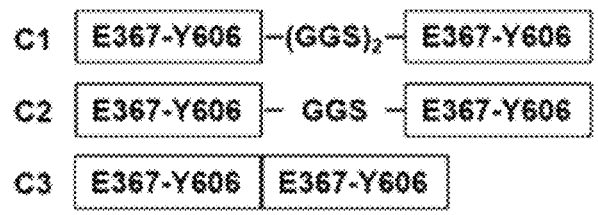

The first design (as shown in FIG. 9A) was as follows:

(1) two GGS linker sequences were added between two repeated tandem (E367-Y606) sequences to obtain MERS-RBD-C1 (abbreviated as C1), where the nucleotide sequence encoding the amino acid sequence was SEQ ID NO: 9.

(2) one GGS linker sequence was added between two repeated tandem (E367-Y606) sequences to obtain MERS-RBD-C2 (abbreviated as C2), where the nucleotide sequence encoding the amino acid sequence is SEQ ID NO: 10;

(3) two repeated (E367-Y606) sequences were directly linked in tandem to obtain MERS-RBD-C3 (abbreviated as C3), where the nucleotide sequence encoding the amino acid sequence is SEQ ID NO: 11.

Figure 9B:
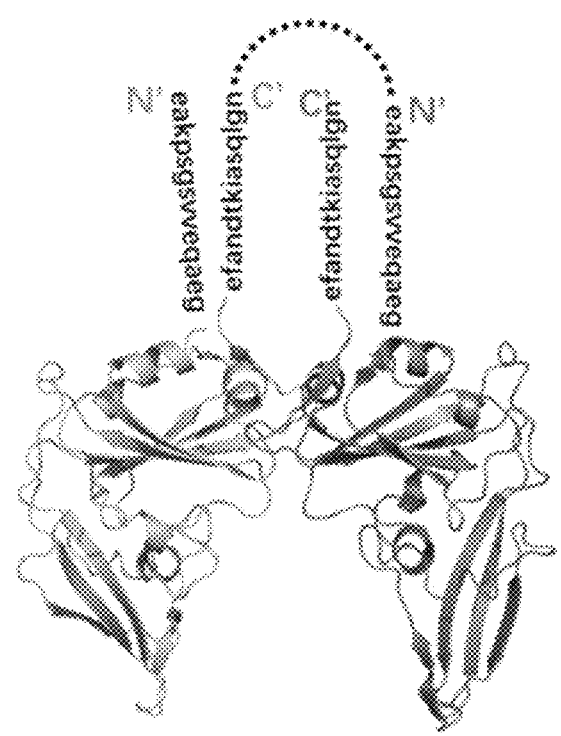

The second design (as shown in FIG. 9B), in order to avoid the effects of cysteine residue (C603) at the position 603 of the C-terminal on expression, a truncated construct at C-terminal residue N602 was conducted, which was specifically as follows:

(4) one GGS linker sequence was added between two repeated tandem (E367-N602) sequences to obtain MERS-RBD-C4 (abbreviated as C4), where the nucleotide sequence encoding the amino acid sequence was SEQ ID NO: 12;

(5) two repeated (E367-N602) sequences were linked in tandem directly to obtain MERS-RBD-C5 (abbreviated as C5), where the nucleotide sequence encoding the amino acid sequence was SEQ ID NO: 13.

Figure 9C:
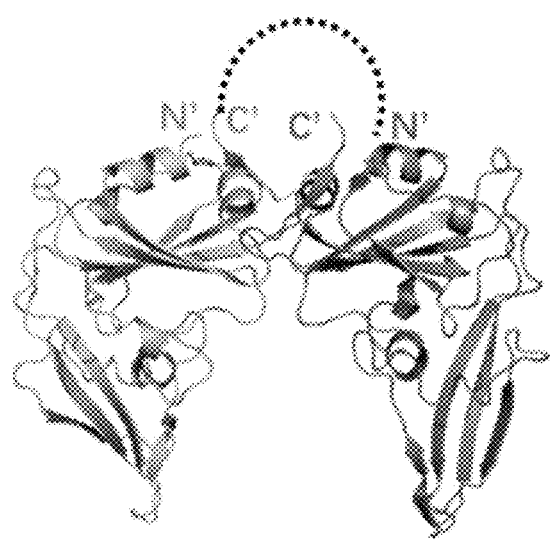
Figure 9C:
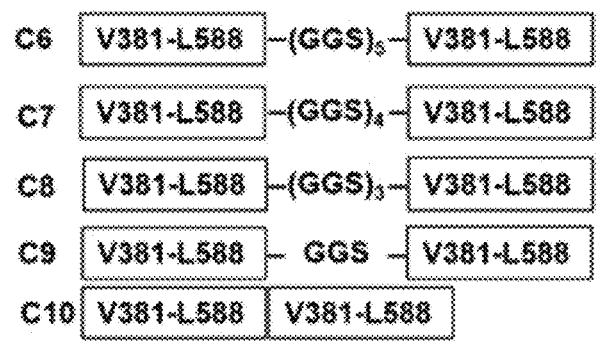

The third design in which (as shown in FIG. 9C) structurally visible sequences were directly expressed and linked by linker sequences of different lengths was specifically as follows:

(6) five GCS linker sequences were added between two repeated tandem (V381-L588) sequences to obtain MERS-RBD-C6 (abbreviated as C6), where the nucleotide sequence encoding the amino acid sequence was SEQ ID NO: 14;

(7) four GCS linker sequences were added between two repeated tandem (V381-L588) sequences to obtain MERS-RBD-C7 (abbreviated as C7), where the nucleotide sequence encoding the amino acid sequence was SEQ ID NO: 15;

(8) three GGS linker sequences were added between two repeated tandem (V381-L588) sequences to obtain MERS-RBD-C8 (abbreviated as C8), where the nucleotide sequence encoding the amino acid sequence was SEQ ID NO: 16;

(9) one GGS linker sequence was added between two repeated tandem (V381-L588) sequences to obtain MERS-RBD-C9 (abbreviated as C9), where the nucleotide sequence encoding the amino acid sequence was SEQ ID NO: 17;

(10) two repeated sequences (V381-L588) were directly linked in tandem to obtain MERS-RBD-C10 (abbreviated as C10), where the nucleotide sequence encoding the amino acid sequence was SEQ ID NO: 18.

Figure 10:
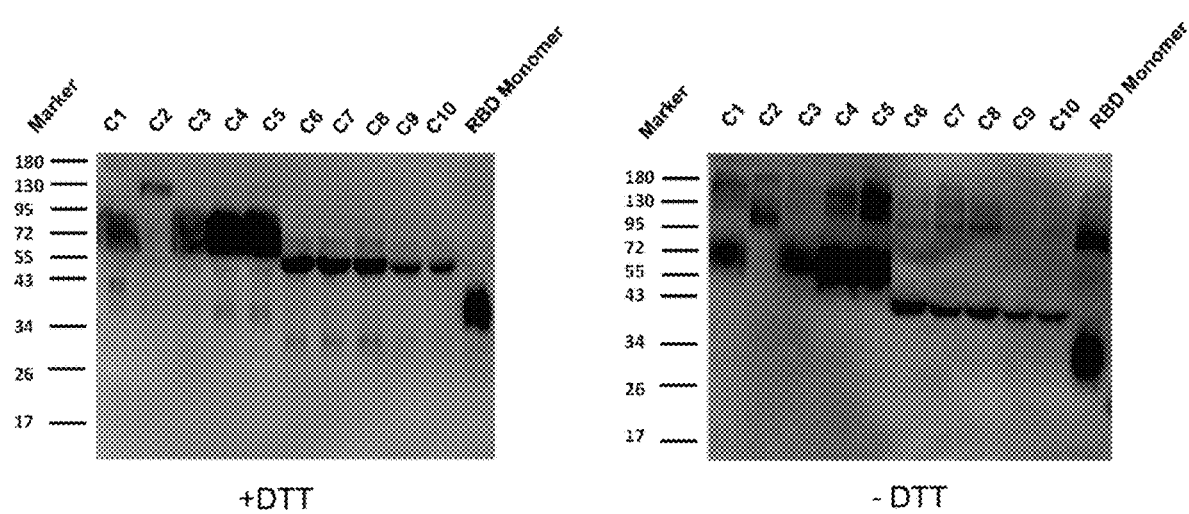
FIG. 10 shows the results of Western blot conducted on MERS-RBD-C1 to MERS-RBD-C10 single-chain dimers expressed in Example 10 under reduced conditions (+DTT) or non-reduced conditions (-DTT), where RBD Monomer is MERS-CoV RBD Monomer protein.

The 5'-terminal of a nucleotide sequence encoding the above VIERS-RBD-C1 to C10 was added with a nucleotide sequence encoding the MERS-S protein self-signal peptide (MIHSVFLLMFLLTPTES), while the 3'-terminal was added with a nucleotide sequence encoding six histidines. A terminator codon was then added to the 3'-terminal, and the obtained nucleotide sequence was inserted between the EcoRI and XhoI restriction enzyme cutting sites of a pCAGGS vector, and a Kozak sequence gccacc was contained upstream of an initiator codon. The above plasmid was transfected into 293T cells, and 48 hours later, the supernatant was collected, and the N-terminus of the protein of interest was provided with a signal peptide. Western blot method was used to detect the expression of the protein of interest, with the results as shown in FIG. 10. The results showed that all constructs were expressed except C2. Under both reduced (+DTT) and non-reduced (−DTT) conditions, the protein was about the size of the dimer (50-60 Kda). Among them, C4 and C5 were expressed at the highest levels. In view of that no any exogenous sequence was introduced and the sequence of the MERS-CoV itself was completely used, the C5 construct would be more advantageous and safer for clinical use. The efficacy of MERS-RBD-C5 as a vaccine would be further assessed.

EXAMPLE 11

Figure 11:
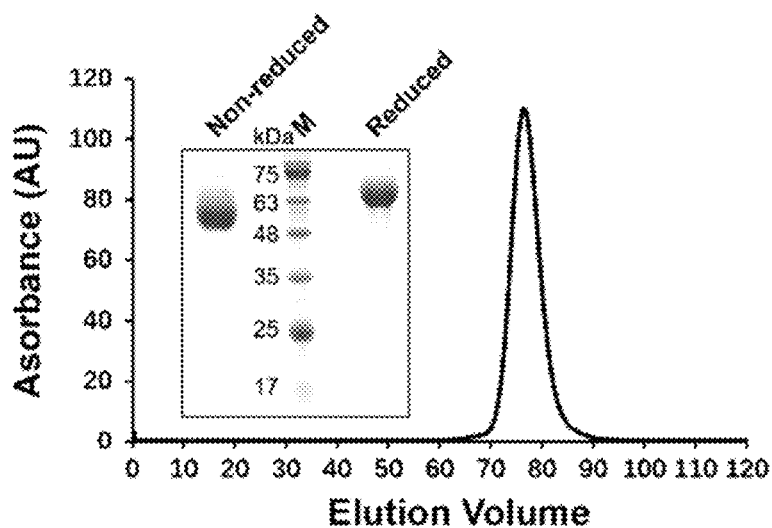
FIG. 11 shows an ultraviolet absorption profile for MERS-RBD-C5 single-chain dirtier expressed in Example 11 subjected to molecular sieve chromatography using a Superdex 200 Hiload 16/60 column (GE), and the results of SDS-PAGE of the purified single-chain dimer under reduced conditions (+DTT) or non-reduced conditions (-DTT).

Mammalian Expression of Single-Chain MERS-CoV RBD Dimer (Sc-RBD Dimer) and Protein Purification MERS-RBD-C5 was expressed using mammalian 293T cells, After transfection of the plasmid into 293T cells, expression was conducted and the supernatant was harvested. The cell supernatant was filtered through a 0.22 μm filtration membrane to remove cell debris. The supernatant of cell culture was purified by Ni affinity chromatography column (Histrap) overnight at 4° C. The resin was washed with buffer A (20 mM Tris, 150 mM NaCl, pH 8.0) to remove non-specific binding proteins. Finally, the protein of interest was eluted from the resin with buffer B (20 mM Tris, 150 mM NaCl, pH 8.0, 300 mM imidazole), and the eluent was concentrated to be within 5 ml with a concentration tube of 10K MWCO. The protein of interest was further purified by molecular sieve chromatography using a Superdex 200 Hiload 16/60 column (GE). The buffer for molecular sieve chromatography was 20 mM Tris and 150 mM NaCl, with pH 8.0. After the molecular sieve chromatography, there was only one main peak near the elution volume of 80 mL. Proteins were collected for SDS-PAGE analysis. As can be seen from the results of SDS-PAGE, MERS-RBD-C5 protein showed a distinct protein band between 55 and 72 kd, which was the size of RBD dimer. It was demonstrated that single-chain MERS-RBD dimer was obtained, as shown in FIG. 11. By using the method of Example 10, 293T cells were used to express and purify the non-single-chain MERS RBD dimer for comparison with the sc-RBD dimer.

EXAMPLE 12

Mice Immunized with Single-Chain MERS-CoV RBD Dimer Sc-RBD Dimer) Protein

The single-chain MERS-RBD dimer antigen obtained in Example 11 was diluted in normal saline and emulsified with adjuvants in groups. Then BALB/c mice aged 4-6 weeks were immunized in groups, with 6 mice in each group. in addition, one group of mice was immunized with PBS as a negative control. A group of mice immunized with 293T cells expressed a non-single-chain form of the dimer. Each mouse received three immunizations of vaccine by intramuscular injection into the thigh, at day 0, day 21 and day 42, respectively, at a vaccination volume of 100 µl each time (containing 10 µg of immunogen). Orbital blood was collected from mice 19 days later after the first immunization, 14 days later after the second immunization and 14 days later after the third immunization. Mouse serum was obtained by centrifugation at 3000 rpm for 10 minutes after standing, and stored in a refrigerator at −20° C. for specific antibody detection and pseudovirus neutralization detection.

Figure 12:
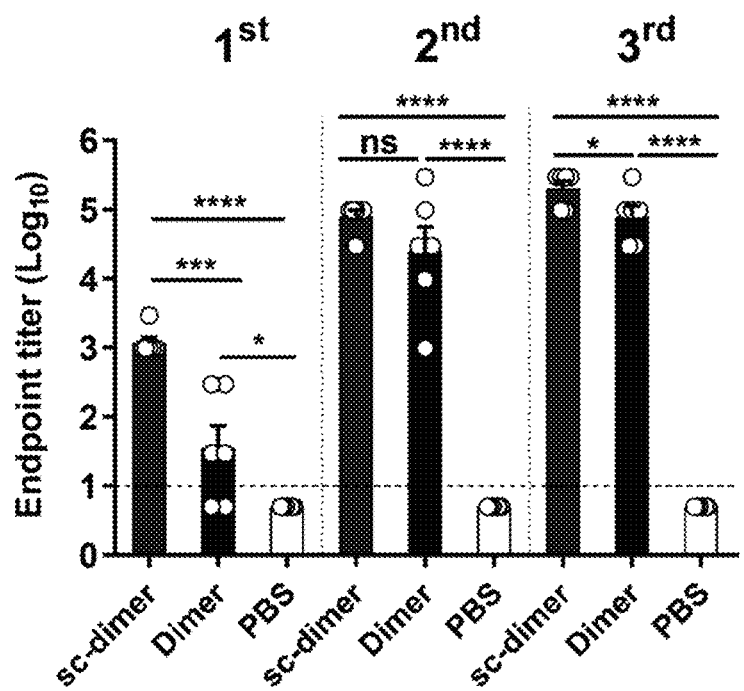
FIG. 12 shows the titers of MERS-CoV-RBD specific IgG antibody elicited by immunization of mice in Example 12 with single-chain MERS-CoV-RBD dimer and disulfide-linked non-single-chain dimer proteins, where sc-dimer is a single-chain dimer, and Dimer is a disulfide-linked non-single-chain dimer. Significant difference analysis: ns, P>0.05; *, P<0.05; *, p<0.001; **, P<0.0001.

The serum specific antibody titer of the mice was detected by ELISA assay, using the method as shown in Example 3, with the results shown in FIG. 12. The RBD-sc-dimer group mice and disulfide-linked non-single-chain RBD-dimer group (indicated by Dimer) mice could be induced to produce antibody response. The titer mean value of the sc-dimer group was higher than that of the Dimer group, and the two groups had a significant difference after three immunizations (*, $P<0.05$). The results showed that the sc-dimer had excellent immunogenicity as the disulfide-linked non-single-chain RBD-dimer.

Figure 13:
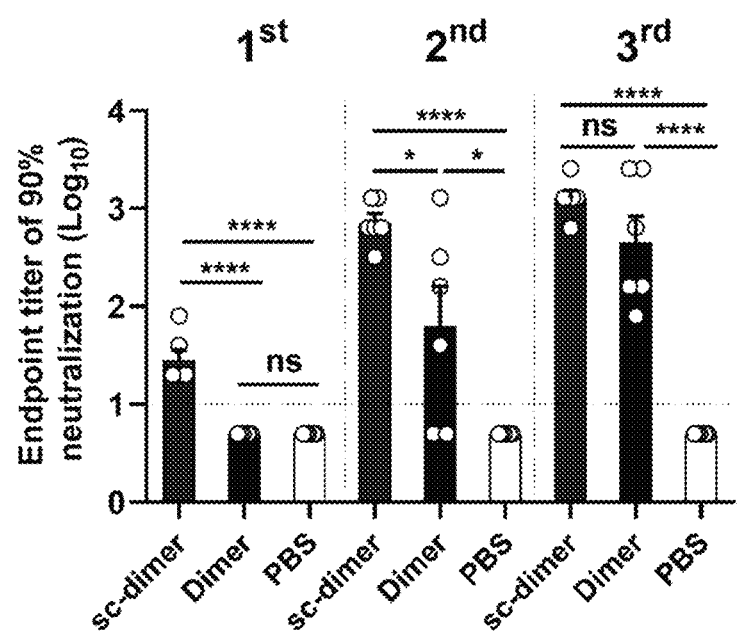
FIG. 13 shows the 90% neutralization titers of antibodies against MERS-CoV pseudovirus elicited by immunization of mice with single-chain MERS-CoV-RBD dimer and disulfide-linked non-single-chain dimer proteins in Example 12, where sc-dimer is a single-chain dimer, and Dimer is a disulfide-linked non-single-chain dimer. Significant difference analysis: ns, P>0.05; *, P<0.05; ****, P<0.0001.

The pseudovirus neutralization experiment was carried out with reference to Example 5, with the results shown in FIG. 13. The sc-dimer group mice and disulfide-linked non-single-chain RBD-dimer group (indicated by Dimer) mice could be induced to produce antibody response. The titer mean value of the sc-dimer group was higher than that of the Dimer group, and there was a significant difference between the two groups after the first immunization and the second immunization (FIG. 13). The mean values of the pseudovirus neutralization titers of sc-dimer group mice after three immunizations were already greater than 1:1000. The results indicated that the vaccine developed by the sc-dimer had great clinical development potential.

EXAMPLE 13

Application of Single-Chain RBD Dimer Technology in Other Coronavirus Vaccines

Figure 14A:
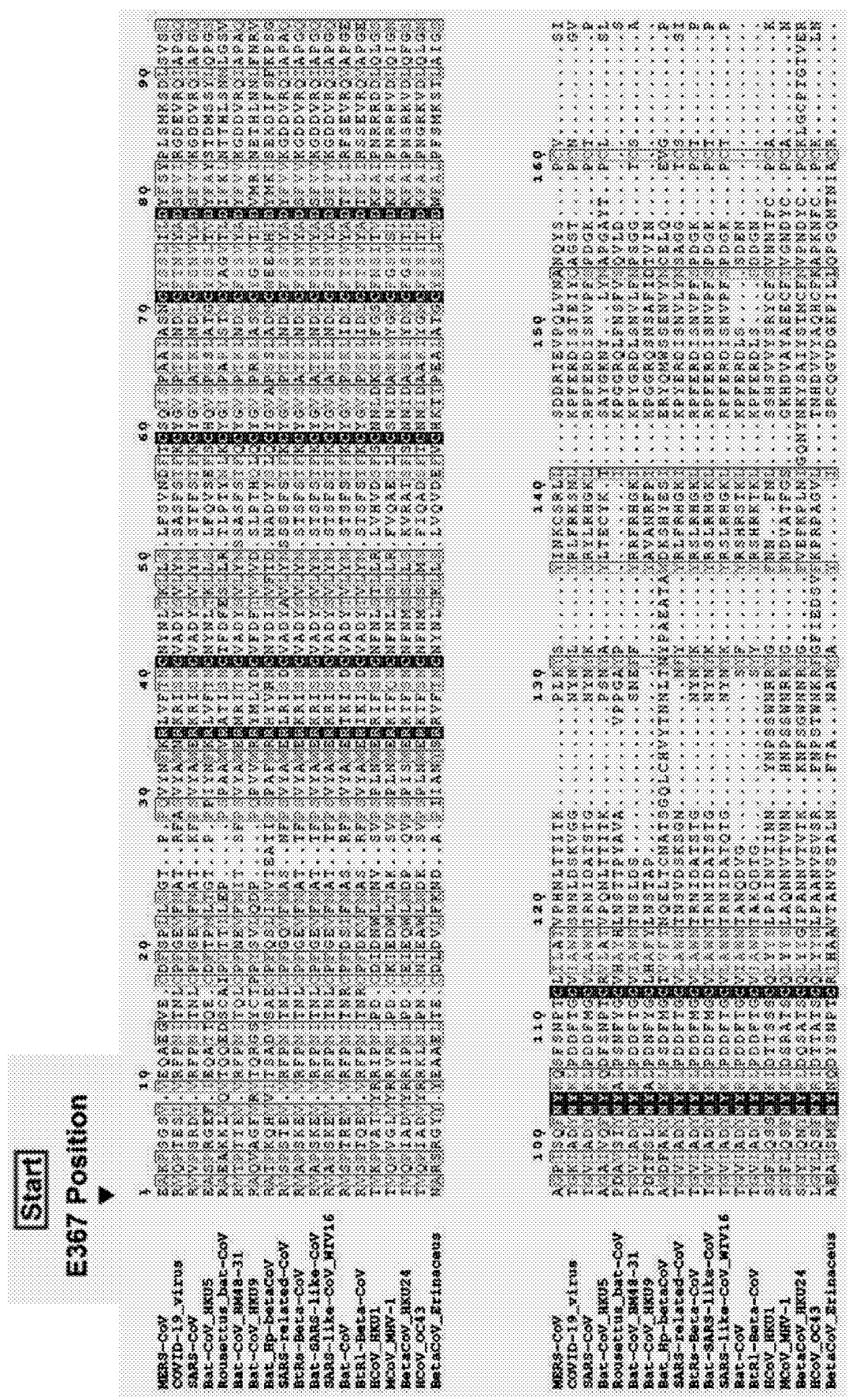
FIGS. 14A and 14B are comparison diagrams of the receptor binding domains (RBDs) of β-coronaviruses in Example 13, where the sequences in the two figures were consecutive, and the following β-coronaviruses were aligned.
Figure 14B:
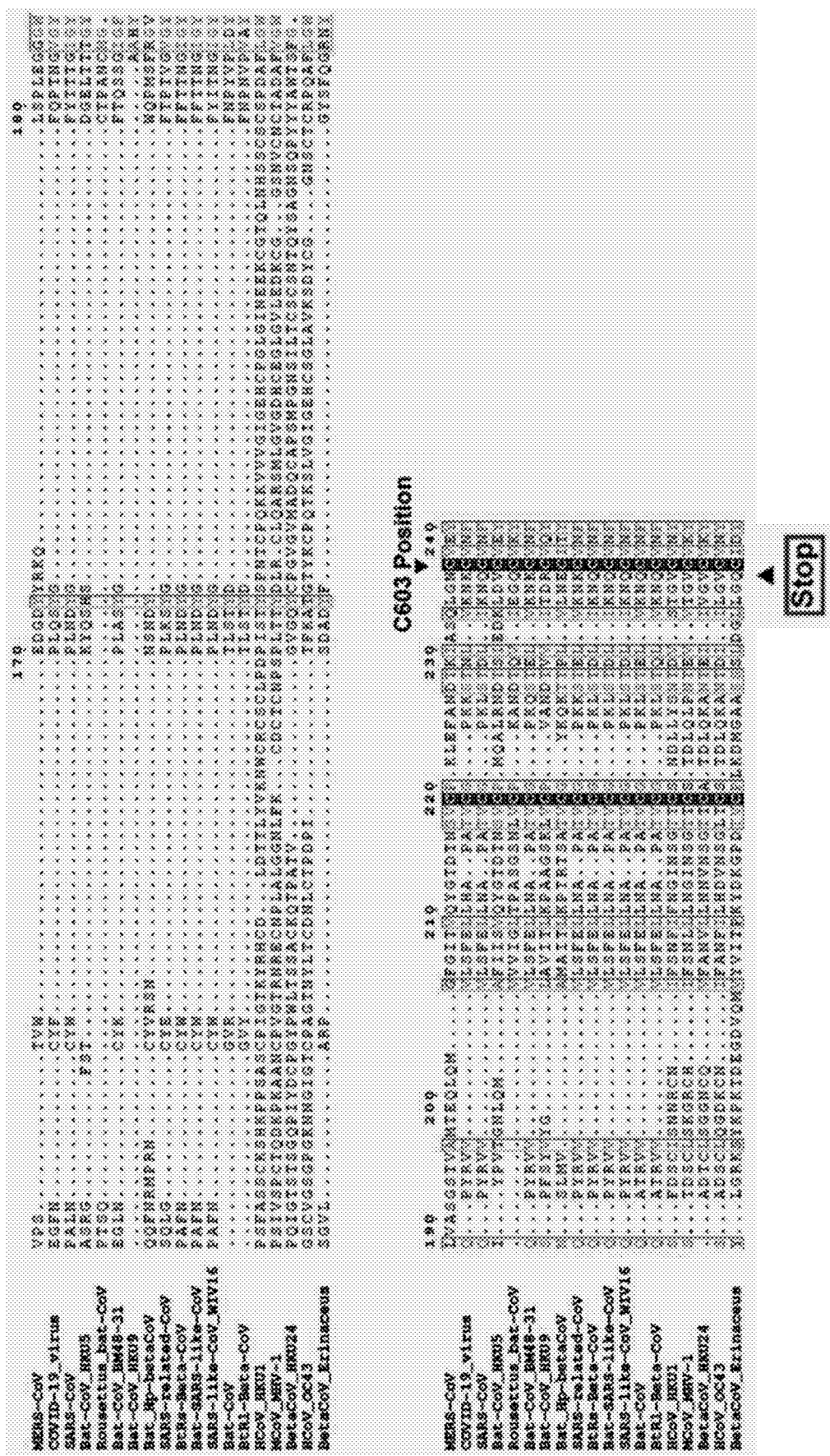

To verify that this concept can be applied to vaccine design of all other coronaviruses, we compared the Receptor Binding Domains (RBDs) of the 19 common βcoronaviruses, the result is shown in FIG. 14A and 14B. All β-coronavirus RBDs exhibited a conserved cysteine at position C603 of MERS-CoV, as shown in FIG. 14B. 2019-nCoV (hereinafter referred to as nCoV) and SARS-CoV were selected for verification. According to the structure of SARS-RBD (PDB: 3D0G), the crystal structure of SARS-RBD was molded into the crystal structure of MERS-RBD dimer at a resolution of 2.8 Å by using Pymol software. A simulated SARS-RBD dimer structure as shown in FIG. 15 was obtained. It was found that, like MERS-RBD dimer. SARS-RBD dimer also existed in the form of end-to-end (as shown in FIG. 15). Since the RBD region of 2019-nCoV shared more than 75% homology with SARS-CoV, it was expected that the RBD dimer of 2019-nCoV would form this end-to-end arrangement. Considering that dimers in MERS-CoV could induce neutralizing antibodies with higher titers than monomers, it was considered that single-chain dimers (sc-dimers) were stilled used to design vaccines. Firstly, based on the S protein sequence of the 2019-nCoV WH01 strain, the construct of three single-chain dimers (sc-dimer) was designed, as shown in FIG. 15: (1) two R319-S530 were linked in tandem and named nCoV-RBD-C1 (the nucleotide sequence encoding the amino acid sequence was SEQ ID NO: 19); (2) two R319-K537 were linked in tandem and named nCoV-RBD-C2 (the nucleotide sequence encoding the amino acid sequence was SEQ ID NO: 20); (3) two R319-F541 were linked in tandem and named nCoV-RBD-C3 (the nucleotide sequence encoding the amino acid sequence was SEQ ID NO: 21); and (4) a further monomer was constructed as R319-F541, named nCoV-RBD-C4 (the nucleotide sequence encoding the amino acid sequence was SEQ ID NO: 22). in addition, a single-chain dimer of SARS-CoV was constructed, and two R306-Q523 were linked in tandem, as shown in FIGS. 14A and 14B, named SARS-CoV-RBD-C1. (the nucleotide sequence encoding this amino acid sequence was SEQ ID NO: 23).

A nucleotide sequence encoding the above nCoV-RBD-C1 to C4 and a nucleotide sequence encoding SARS-CoV-RBD-C1 (SEQ. ID NO: 23) were added with the nucleotide sequence encoding the MERS-S protein self-signal peptide (MIHSVFLLMFLLPTES). After the nucleotide sequence encoding six histidines was added to the 3'-terminal, a terminator codon was added to the 3'-terminal, and inserted into the pCAGGS vector EcoRI and XhoI restriction enzyme cutting sites, and the Kozak sequence gccacc was contained upstream of the initiator codon thereof. The above plasmid was transfected into 293T cells. The supernatant was harvested 48 hours later and the expression of the protein of interest was detected by Western blot. The expression results are shown in FIG. 16. The results showed that the expression of nCoV-RBD-C2 was the highest among several antigen designs of 2019-nCoV. The SARS-CoV-RBD-C1 construct also had a high protein expression.

The above results indicated that in the design of a single-chain dimer of the β-coronavirus, the optimal construct is from the first amino acid of FIG. 14A (marked as Start) to an amino acid before the last cysteine of FIG. 14B (marked as Stop).

EXAMPLE 14

Expression and Purification of Single-Chain 2019-nCoV-RBD Dimer Antigen and Single-Chain SARS-CoV-RBD Dimer Antigen Mammalian 293T cells were used to express nCoV-RBD-C2. After the plasmid was transfected into 293T cells, the supernatant was harvested. The cell supernatant was filtered through a 0.22 µm filtration membrane to remove cell debris. The supernatant of cell culture was purified by Ni affinity chromatography column (Histrap) overnight at 4° C. The resin was washed with buffer A (20 mM Tris, 150 mM NaCl, pH 8.0) to remove non-specific binding proteins. Finally, the protein of interest was eluted from the resin with buffer B (20 mM Tris, 150 mM NaCl, pH 8.0, 300 mM imidazole), and the eluent was concentrated to be within 5 ml with a concentration tube of 10K MWCO. The protein of interest was further purified by molecular sieve chromatography with a Superdex 200 Hiload 16/60 column (GE). The buffer for molecular sieve chromatography was 20 mM Tris and 150 mM NaCl, with PH 8.0. After molecular sieve chromatography, there was only one main peak near the elution volume of 80 ml. Proteins were collected for SDS-PAGE analysis. As can be seen from the results of SDS-PAGE, nCoV-RBD-C2 protein showed a distinct protein band between 48-63 kd, which was the size of RBD-dimer. It was demonstrated that single-chain 2019-nCoV-RBD dimer was obtained, as shown in FIG. 17. The purity was more than 9.5%. The results showed that such construct could produce sufficient and high-purity single-chain 2019-nCoV dimer protein.

The monomeric RBD protein of 2019-nCoV (obtained by expression of nCoV-RBD-C4 construct), the monomeric RBD protein of SARS-CoV (SARS-CoV RBD R306-F527, having an amino acid sequence and a nucleotide sequence encoding the amino acid sequence as shown as SEQ ID NO: 26 and SEQ ID NO: 27) and the single-chain dimer protein of SARS-CoV (obtained by expression of SARS-CoV-RBD-C1 construct) were expressed and purified in the same way.

As shown in FIG. 18, the result of the single-chain dimer protein of SARS-CoV showed that after the molecular sieve chromatography, there was only one main peak near the elution volume of 80 mL. Proteins were collected for SDS-PAGE analysis. As can be seen from the results of SDS-PAGE, SARS-CoV-RBD-C1 protein of interest showed a distinct protein band between 55 and72 kd, which was the size of RBD-dimer. It was demonstrated that single-chain SARS-RBD dimer was obtained, as shown in FIG. 18, and with high purity.

EXAMPLE 15

Mice Immunized with Single-Chain 2019-nCoV-RBD Dimer Protein

The single-chain 2019-nCoV-RBD dimer and 2019-nCoV-RBD monomer obtained in Example 14 was diluted in PBS solution and emulsified with AddaVax adjuvant in groups. Then BALB/c mice (average body weight 15-20g, the same applies below) aged 6-8 weeks were immunized in groups, with 8 mice in each group. Each mouse received three immunizations of vaccine by intramuscular injection into the thigh, at day 0, day 21 and day 42, respectively, at a vaccination volume of 100 µl each time (containing 10 µg of immunogen). Blood samples were collected from mice 19 days later after the first immunization, 14 days later after the second immunization and 14 days later after the third immunization. Mouse senior was obtained by centrifugation at 3000 rpm for 10 minutes after standing, and stored in a refrigerator at −20° C. for specific antibody detection and pseudovirus neutralization detection.

The serum specific antibody titer of 2019-CoV RBD of the mice was detected by ELISA assay, using the method as shown in Example 3, with the results shown in FIG. 19. The single-chain dimeric RBD (indicated by sc-dimer) and monomeric RBD (indicated by Monomer) could induce mice to produce antibody response. The titer mean value of the single-chain dimetic RBD group was higher than that of the monomeric RBD group, and the two groups had a significant difference after three immunizations (FIG. 19). The single-chain dimeric RBD induced mice to produce antibodies at levels of up to approximately $1:10^6$ after three immunizations. The results showed that the immunogenicity of the single-chain dimeric RBD antigen was stronger than that of the single-chain dimeric RBD antigen, and it had great potential as a potential new coronavirus vaccine.

2019-nCoV pseudovirus neutralization assay was carry out with reference to Example 5, with results as shown in FIG. 20. Neutralizing antibodies were induced in only the single-chain dimeric RBD (indicated by sc-dimer) group after the first immunization. Neutralizing antibodies were not detected in both the monomeric RBD (indicated by Monomer) and PBS groups, and there was a significant difference of neutralizing antibody titers between the single-chain dimeric RBD group and the monomeric RBD group (FIG. 20). After the second and third immunizations, both single-chain dimeric RBD and monomeric RBD could induce mice to produce neutralizing antibodies. After each immunization, the mean value of neutralizing antibody titers of the single-chain dimeric RBD group was higher than that of the monomeric RBD group (10-100 times higher), and there was a significant difference between the two groups after each immunization (FIG. 20). The single-chain dimeric RBD induced mice to produce antibodies at levels of up to approximately $1:10^4$ after three immunizations. The results showed that the single-chain dimeric RBD antigen could induce mice to produce higher neutralizing antibody level than the monomeric RBD antigen, and the single-chain dimeric RBD antigen had high advantages in use.

Neutralization assay was conducted with serum after the second immunization for 2019-nCoV euvirus (2020XN4276 strain, which was published in Lu J, du Plessis L, Liu Z, et al. Genomic Epidemiology of SARS-CoV-2 in Guangdong Province, China. Cell. 2020;181(5):997-1003.e9. doi: 10.1016/j.cell.2020.04.023, provided by Guangdong Provincial Center for Disease Control and Prevention). The experimental results are shown in FIG. 21. The results showed that the RBD dimer could induce mice to produce high levels of neutralizing antibodies against the novel coronavirus. The highest neutralizing NT50 was greater than 4096, and the lowest NT50 was 512 in a mouse. However, the neutralizing antibodies against the novel coronavirus were: detected in only 2 of the 8 mice in the RBD monomer group, with lower NT50, which were 128 and 256, respectively. The results indicated that the dimeric RBD could induce mice to produce higher levels of neutralizing antibodies against the novel coronavirus.

EXAMPLE 16

Mice Immunized with Single-Chain SARS-RBD Dimer Protein

The single-chain SARS-RBD dimer and SARS-RBD monomer obtained in Example 14 were diluted in PBS solution and emulsified with AddaVax adjuvant in groups. Then BALB/c mice aged 6-8 weeks were immunized in groups, with 6 mice in each group. Each mouse received three immunizations of vaccine by intramuscular injection into the thigh, at day 0, day 2 and day 42, respectively, at a vaccination volume of 100 µl each time (containing 10 µg of immunogen). Blood samples were collected from mice 19 days later after the first immunization, 14 days later after the second immunization and 14 days later after the third immunization. Mouse serum was obtained by centrifugation at 3000 rpm for 10 minutes after standing, and stored in a refrigerator at −20° C. for specific antibody detection and pseudovirus neutralization detection.

The serum specific antibody titer of SARS-RBD of the mice was detected by ELISA assay, using the method shown in Example 3, with the results shown in FIG. 22. The single-chain dimeric RBD (indicated by sc-dimer) and monomeric RBD (indicated by Monomer) could induce mice to produce antibody response. The titer mean value of the single-chain dimeric RBD group was higher than that of the monomeric RBD group, and the two groups had a significant difference after the second and the third immunizations (FIG. 22). The dimeric RBD induced mice to produce antibodies at levels of up to approximately $1:10^6$ after three immunizations. The results showed that the immunogenicity of the dimeric RBD antigen was stronger than that of the monomeric RBD antigen.

The neutralization assay was conducted for SARS-CoV pseudovirus with reference to Example 5, with the results shown in FIG. 23. After the first and second immunizations, both dimeric RBD (indicated by sc-dimer) group and monomeric RBD (indicated by Monomer) group could induce mice to produce neutralizing antibodies. The mean value of neutralizing antibody titers of the dimeric RBD group was higher, and there was a significant difference between the two groups (FIG. 23). After the third immunization, the mean value of neutralizing antibody titers of the dimeric RBD group was still higher than that of the monomeric RBD group, and there was a significant difference (FIG. 23). The levels of neutralizing antibodies induced by dimeric RBD in mice after three immunizations were higher than $1:10^3$. The results showed that the dimeric RBD antigen could induce mice to produce higher neutralizing antibody level than the monomeric RBD antigen, and the dimeric RBD antigen had high advantages in use.

Finally, it should be noted that the above examples are only intended to illustrate rather than limit the technical solutions of the present disclosure. Although the present disclosure has been described in detail with reference to the foregoing examples, it will be understood by a person skilled in the art that the technical solutions described in the foregoing examples may still be modified, or some technical features may be equivalently replaced; and such modifications or substitutions do not depart from the spirit and scope of the corresponding technical solutions of the examples of the present disclosure.

INDUSTRIAL PRACTICAL APPLICABILITY

The examples of the present disclosure relate to antigens of β-coronaviruses, preparation methods and uses thereof. An antigen of a β-coronavirus, its amino acid sequence comprises an amino acid sequence arranged in a (A-B)-(A-B) pattern or an amino acid sequence arranged in a (A-B)-C-(A-B) pattern or an amino acid sequence arranged in a (A-B)-(A-B') pattern or an amino acid sequence arranged in a (A-B)-C-(A-B') pattern, where A-B represents a partial amino acid sequence or the entire amino acid sequence of a receptor binding domain of a surface spike protein of the β-coronavirus; C represents an amino acid linker sequence; A-B' represents an amino acid sequence obtained by substitution, deletion or addition of one or more amino acids in the amino acid sequence of A-B; a protein encoded by A-B' has the identical or substantially identical immunogenicity as a protein encoded by A-B; and the antigen of the β-coronavirus has a single-chain dimer structure. The single-chain dimer expressed according to the examples of the present disclosure is stable in content and has excellent immunogenicity as an antigen of a β-coronavirus, and the vaccine prepared by using the single-chain dimer as an antigen of a β-coronavirus can elicit high-titer neutralizing antibodies in mice.

What is claimed is:

1. An antigen of a β-coronavirus, its amino acid comprising an amino acid sequence arranged in a (A-B)-(A-B) pattern or an amino acid sequence arranged in a (A-B)-C-(A-B) pattern or an amino acid sequence arranged in a (A-B)-(A-B') pattern or an amino acid sequence arranged in a (A-B)-C-(A-B') pattern, wherein A-B represents a partial amino acid sequence or an entire amino acid sequence of a receptor binding domain of a surface spike protein of the β-coronavirus; C represents an amino acid linker sequence; A-B' represents an amino acid sequence obtained by substitution, deletion or addition of one or more amino acids in the amino acid sequence of A-B; a protein encoded by A-B' has an identical immunogenicity as a protein encoded by A-B; and the antigen of the β-coronavirus has a single-chain dimer structure.

2. The antigen of the β-coronavirus according to claim 1, wherein the β-coronavirus is selected from a group consisting of severe respiratory syndrome coronavirus, Middle East respiratory syndrome coronavirus, and 2019 novel coronavirus.

3. The antigen of the β-coronavirus according to claim 1, wherein the amino acid linker sequence comprises a $(GGS)_n$ linker sequence, wherein n represents the number of GGSs, n is an integer more than or equal to 1; preferably, n is an integer selected from 1 to 10, and further preferably, n is an integer selected from 1 to 5.

4. The antigen of the β-coronavirus according to claim 1, wherein the partial amino acid sequence of the receptor binding domain of the surface spike protein of the β-coronavirus is at least 50%, 60%, 70%, 80%, 90%, 95%, or 99% of the entire amino acid sequence of the receptor binding domain of the surface spike protein of the β-coronavirus.

5. The antigen of the β-coronavirus according to claim 1, wherein:
when the β-coronavirus is the Middle East respiratory syndrome coronavirus, the partial or the entire amino acid sequence of the receptor binding domain of the surface spike protein thereof is any one selected from a group consisting of following amino acid sequences:
(1) SEQ ID NO: 1, SEQ ID NO: 2, or SEQ ID NO: 3;
(2) an amino acid sequence obtained by substitution, deletion or addition of one or more amino acids in the amino acid sequence (1), wherein a protein encoded by the amino acid sequence has an identical immunogenicity as a protein encoded by the amino acid sequence (1); alternatively, the partial amino acid sequence of the receptor binding domain of the surface spike protein thereof comprises SEQ ID NO: 2;
when the β-coronavirus is the 2019 novel coronavirus, the partial or the entire amino acid sequence of the receptor binding domain of the surface spike protein thereof is any one selected from a group consisting of following amino acid sequences:
(3) SEQ ID NO: 5, SEQ ID NO: 6, or SEQ ID NO: 7;
(4) an amino acid sequence obtained by substitution, deletion or addition of one or more amino acids in the amino acid sequence (3), wherein a protein encoded by the amino acid sequence has an identical immunogenicity as a protein encoded by the amino acid sequence (3);
alternatively, the partial amino acid sequence of the receptor binding domain of the surface spike protein comprises SEQ ID NO: 6; and when the β-coronavirus is the severe respiratory syndrome coronavirus, the partial or the entire amino acid sequence of the receptor binding domain of the surface spike protein thereof is any one selected from a group consisting of following amino acid sequences:
(5) SEQ ID NO: 8;
(6) an amino acid sequence obtained by substitution, deletion or addition of one or more amino acids in the amino acid sequence (5), wherein a protein encoded by the amino acid sequence has an identical immunogenicity as a protein encoded by the amino acid sequence (5).

6. The antigen of the β-coronavirus according to claim 5, wherein:
when the β-coronavirus is the Middle East respiratory syndrome coronavirus, the amino acid sequence of the antigen of the β-coronavirus comprises any one selected from a group consisting of following amino acid sequences:
(1) two repeated amino acid sequences of SEQ ID NO: 1 linked in tandem by a GGSGGS linker sequence;
(2) two repeated amino acid sequences of SEQ ID NO: 1 linked in tandem by a GGS linker sequence;
(3) two repeated amino acid sequences of SEQ ID NO: 1 linked directly in tandem;
(4) two repeated amino acid sequences of SEQ ID NO: 2 linked in tandem by a GGS linker sequence;
(5) two repeated amino acid sequences of SEQ ID NO: 2 linked directly in tandem;
(6) two repeated amino acid sequences of SEQ ID NO: 3 linked by a GGSGGSGGSGS linker sequence;
(7) two repeated amino acid sequences of SEQ ID NO: 3 linked in tandem by a GGSGGSGGSGS linker sequence;
(8) two repeated amino acid sequences of SEQ ID NO: 3 linked in tandem by a GGSGGSGGS linker sequence;
(9) two repeated amino acid sequences of SEQ ID NO: 3 linked in tandem by a GGS linker sequence; and
(10) two repeated amino acid sequences of SEQ ID NO: 3 linked directly in tandem;
alternatively, the amino acid sequence of the antigen of the β-coronavirus comprises two repeated amino acid sequences of SEQ ID NO: 2 directly linked in tandem;
when the β-coronavirus is the 2019 novel coronavirus, the amino acid sequence of the antigen of the β-coronavirus comprises any one selected from a group consisting of following amino acid sequences:
(1) two repeated amino acid sequences of SEQ ID NO: 5 linked directly in tandem;
(2) two repeated amino acid sequences of SEQ ID NO: 6 linked directly in tandem; and
(3) two repeated amino acid sequences of SEQ ID NO: 7 linked directly in tandem;
alternatively, the amino acid sequence of the antigen of the β-coronavirus comprises two repeated amino acid sequences of SEQ ID NO: 6 directly linked in tandem; and
when the β-coronavirus is the severe respiratory syndrome coronavirus, the amino acid sequence of the antigen of the β-coronavirus comprises two repeated amino acid sequences of SEQ ID NO: 8 linked directly in tandem.

7. The antigen of the β-coronavirus according to claim 6, wherein:
a nucleotide sequence encoding the two repeated amino acid sequences of SEQ ID NO: 1 linked in tandem by the GGSGGS linker sequence is shown as SEQ ID NO: 9;

a nucleotide sequence encoding the two repeated amino acid sequences of SEQ ID NO: 1 linked in tandem by the GGS linker sequence is shown as SEQ ID NO: 10;

a nucleotide sequence encoding the two repeated amino acid sequences of SEQ ID NO: 1 linked directly in tandem is shown as SEQ ID NO: 11;

a nucleotide sequence encoding the two repeated amino acid sequences of SEQ ID NO: 2 linked in tandem by the GGS linker sequence is shown as SEQ ID NO: 12;

a nucleotide sequence encoding the two repeated amino acid sequences of SEQ ID NO: 2 linked directly in tandem is shown as SEQ ID NO: 13;

a nucleotide sequence encoding the two repeated amino acid sequences of SEQ ID NO: 3 linked in tandem by the GGSGGSGGSGGSGGS linker sequence is shown as SEQ ID NO: 14;

a nucleotide sequence encoding the two repeated amino acid sequences of SEQ ID NO: 3 linked in tandem by the GGSGGSGGSGGS linker sequence is shown as SEQ ID NO: 15;

a nucleotide sequence encoding the two repeated amino acid sequences of SEQ ID NO: 3 linked in tandem by the GGSGGSGGS linker sequence is shown as SEQ ID NO: 16;

a nucleotide sequence encoding the two repeated amino acid sequences of SEQ ID NO: 3 linked in tandem by the GGS linker sequence is shown as SEQ ID NO: 17;

a nucleotide sequence encoding the two repeated amino acid sequences of SEQ ID NO: 3 linked directly in tandem is shown as SEQ ID NO: 18;

a nucleotide sequence encoding the two repeated amino acid sequences of SEQ ID NO: 5 linked directly in tandem is shown as SEQ ID NO: 19;

a nucleotide sequence encoding the two repeated amino acid sequences of SEQ ID NO: 6 linked directly in tandem is shown as SEQ ID NO: 20;

a nucleotide sequence encoding the two repeated amino acid sequences of SEQ ID NO: 7 linked directly in tandem is shown as SEQ ID NO: 21; and a nucleotide sequence encoding the two repeated amino acid sequences of SEQ ID NO: 8 linked directly in tandem is shown as SEQ ID NO: 23.

8. A method for preparing the antigen of the β-coronavirus according to claim 1, comprising following steps: adding a sequence encoding a signal peptide to a 5'-terminal of a nucleotide sequence encoding the antigen of the β-coronavirus, adding a terminator codon to a 3'-terminal for cloning and expression, screening a correct recombinant, transfecting an expression system cell for expression, collecting a cell supernatant after expression, and purifying to obtain the antigen of the β-coronavirus.

9. The method according to claim 8, wherein the expression system cell is selected from a group consisting of mammalian cell, insect cell, yeast cell, and bacterial cell; preferably, the mammalian cell is 293T cell or CHO cell, and the bacterial cell is *Escherichia coli* cell.

10. A nucleotide sequence encoding the antigen of the β-coronavirus according to claim 1.

11. A recombinant vector comprising the nucleotide sequence according to claim 10.

12. An expression system cell comprising the recombinant vector according to claim 11.

13. A method for preparing a vaccine against the β-coronavirus by using the antigen of the β-coronavirus according to claim 1.

14. A β-coronavirus vaccine, comprising the antigen of the β-coronavirus according to claim 1 and an adjuvant.

15. The β-coronavirus vaccine according to claim 14, wherein the adjuvant is selected from a group consisting of an aluminum adjuvant, an MF59 adjuvant, and an MF59-like adjuvant.

16. A β-coronavirus DNA vaccine, comprising a recombinant vector comprising a DNA sequence encoding the antigen of the β-coronavirus according to claim 1.

17. A β-coronavirus RNA vaccine, comprising a recombinant vector comprising an mRNA sequence encoding the antigen of the β-coronavirus according to claim 1.

18. A β-coronavirus viral vector vaccine comprising a recombinant viral vector comprising a nucleotide sequence encoding the antigen of the β-coronavirus according to claim 1, alternatively, the viral vector is one or more selected from a group consisting of an adenovirus vector, a poxvirus vector, an influenza virus vector, and an adeno-associated virus vector.

19. A method for preparing a vaccine against the β-coronavirus by using the nucleotide sequence according to claim 10.

20. A method for preparing a vaccine against the β-coronavirus by using the recombinant vector according to claim 11.

21. A method for preparing a vaccine against the β-coronavirus by using the expression system cell according to claim 12.

* * * * *

SEQUENCE LISTING

```
<160> NUMBER OF SEQ ID NOS: 27

<210> SEQ ID NO 1
<211> LENGTH: 240
<212> TYPE: PRT
<213> ORGANISM: Betacoronavirus/Middle East respiratory syndrome-related
      coronavirus

<400> SEQUENCE: 1

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
            20                  25                  30

Phe Lys Arg Leu Val Phe Thr Asn Cys Asn Tyr Asn Leu Thr Lys Leu
        35                  40                  45

Leu Ser Leu Phe Ser Val Asn Asp Phe Thr Cys Ser Gln Ile Ser Pro
    50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125
```

```
Leu Lys Tyr Ser Tyr Ile Asn Lys Cys Ser Arg Leu Leu Ser Asp Asp
            130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu Glu Phe
    210                 215                 220

Ala Asn Asp Thr Lys Ile Ala Ser Gln Leu Gly Asn Cys Val Glu Tyr
225                 230                 235                 240

<210> SEQ ID NO 2
<211> LENGTH: 236
<212> TYPE: PRT
<213> ORGANISM: Betacoronavirus/Middle East respiratory syndrome-related
      coronavirus

<400> SEQUENCE: 2

Glu Ala Lys Pro Ser Gly Ser Val Val Glu Gln Ala Glu Gly Val Glu
1               5                   10                  15

Cys Asp Phe Ser Pro Leu Leu Ser Gly Thr Pro Pro Gln Val Tyr Asn
            20                  25                  30

Phe Lys Arg Leu Val Phe Thr Asn Cys Asn Tyr Asn Leu Thr Lys Leu
        35                  40                  45

Leu Ser Leu Phe Ser Val Asn Asp Phe Thr Cys Ser Gln Ile Ser Pro
    50                  55                  60

Ala Ala Ile Ala Ser Asn Cys Tyr Ser Ser Leu Ile Leu Asp Tyr Phe
65                  70                  75                  80

Ser Tyr Pro Leu Ser Met Lys Ser Asp Leu Ser Val Ser Ser Ala Gly
                85                  90                  95

Pro Ile Ser Gln Phe Asn Tyr Lys Gln Ser Phe Ser Asn Pro Thr Cys
            100                 105                 110

Leu Ile Leu Ala Thr Val Pro His Asn Leu Thr Thr Ile Thr Lys Pro
        115                 120                 125

Leu Lys Tyr Ser Tyr Ile Asn Lys Cys Ser Arg Leu Leu Ser Asp Asp
    130                 135                 140

Arg Thr Glu Val Pro Gln Leu Val Asn Ala Asn Gln Tyr Ser Pro Cys
145                 150                 155                 160

Val Ser Ile Val Pro Ser Thr Val Trp Glu Asp Gly Asp Tyr Tyr Arg
                165                 170                 175

Lys Gln Leu Ser Pro Leu Glu Gly Gly Gly Trp Leu Val Ala Ser Gly
            180                 185                 190

Ser Thr Val Ala Met Thr Glu Gln Leu Gln Met Gly Phe Gly Ile Thr
        195                 200                 205

Val Gln Tyr Gly Thr Asp Thr Asn Ser Val Cys Pro Lys Leu Glu Phe
    210                 215                 220

Ala Asn Asp Thr Lys Ile Ala Ser Gln Leu Gly Asn
225                 230                 235

<210> SEQ ID NO 3
<211> LENGTH: 208
```

```
<212> TYPE: PRT
<213> ORGANISM: Betacoronavirus/Middle East respiratory syndrome-related
      coronavirus

<400> SEQUENCE: 3

Val Glu Cys Asp Phe Ser Pro Leu Leu Ser Gly Thr Pro Pro Gln Val
1               5                   10                  15

Tyr Asn Phe Lys Arg Leu Val Phe Thr Asn Cys Asn Tyr Asn Leu Thr
            20                  25                  30

Lys Leu Leu Ser Leu Phe Ser Val Asn Asp Phe Thr Cys Ser Gln Ile
        35                  40                  45

Ser Pro Ala Ala Ile Ala Ser Asn Cys Tyr Ser Ser Leu Ile Leu Asp
50                  55                  60

Tyr Phe Ser Tyr Pro Leu Ser Met Lys Ser Asp Leu Ser Val Ser Ser
65                  70                  75                  80

Ala Gly Pro Ile Ser Gln Phe Asn Tyr Lys Gln Ser Phe Ser Asn Pro
                85                  90                  95

Thr Cys Leu Ile Leu Ala Thr Val Pro His Asn Leu Thr Thr Ile Thr
            100                 105                 110

Lys Pro Leu Lys Tyr Ser Tyr Ile Asn Lys Cys Ser Arg Leu Leu Ser
        115                 120                 125

Asp Asp Arg Thr Glu Val Pro Gln Leu Val Asn Ala Asn Gln Tyr Ser
130                 135                 140

Pro Cys Val Ser Ile Val Pro Ser Thr Val Trp Glu Asp Gly Asp Tyr
145                 150                 155                 160

Tyr Arg Lys Gln Leu Ser Pro Leu Glu Gly Gly Gly Trp Leu Val Ala
                165                 170                 175

Ser Gly Ser Thr Val Ala Met Thr Glu Gln Leu Gln Met Gly Phe Gly
            180                 185                 190

Ile Thr Val Gln Tyr Gly Thr Asp Thr Asn Ser Val Cys Pro Lys Leu
        195                 200                 205

<210> SEQ ID NO 4
<211> LENGTH: 211
<212> TYPE: PRT
<213> ORGANISM: Betacoronavirus/Middle East respiratory syndrome-related
      coronavirus

<400> SEQUENCE: 4

Glu Gly Val Glu Cys Asp Phe Ser Pro Leu Leu Ser Gly Thr Pro Pro
1               5                   10                  15

Gln Val Tyr Asn Phe Lys Arg Leu Val Phe Thr Asn Cys Asn Tyr Asn
            20                  25                  30

Leu Thr Lys Leu Leu Ser Leu Phe Ser Val Asn Asp Phe Thr Cys Ser
        35                  40                  45

Gln Ile Ser Pro Ala Ala Ile Ala Ser Asn Cys Tyr Ser Ser Leu Ile
50                  55                  60

Leu Asp Tyr Phe Ser Tyr Pro Leu Ser Met Lys Ser Asp Leu Ser Val
65                  70                  75                  80

Ser Ser Ala Gly Pro Ile Ser Gln Phe Asn Tyr Lys Gln Ser Phe Ser
                85                  90                  95

Asn Pro Thr Cys Leu Ile Leu Ala Thr Val Pro His Asn Leu Thr Thr
            100                 105                 110

Ile Thr Lys Pro Leu Lys Tyr Ser Tyr Ile Asn Lys Cys Ser Arg Leu
        115                 120                 125
```

Leu Ser Asp Asp Arg Thr Glu Val Pro Gln Leu Val Asn Ala Asn Gln
            130                 135                 140

Tyr Ser Pro Cys Val Ser Ile Val Pro Ser Thr Val Trp Glu Asp Gly
145                 150                 155                 160

Asp Tyr Tyr Arg Lys Gln Leu Ser Pro Leu Glu Gly Gly Gly Trp Leu
                165                 170                 175

Val Ala Ser Gly Ser Thr Val Ala Met Thr Glu Gln Leu Gln Met Gly
            180                 185                 190

Phe Gly Ile Thr Val Gln Tyr Gly Thr Asp Thr Asn Ser Val Cys Pro
        195                 200                 205

Lys Leu Glu
    210

<210> SEQ ID NO 5
<211> LENGTH: 212
<212> TYPE: PRT
<213> ORGANISM: Betacoronavirus/SARS-CoV-2

<400> SEQUENCE: 5

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser
    210

<210> SEQ ID NO 6
<211> LENGTH: 219
<212> TYPE: PRT
<213> ORGANISM: Betacoronavirus/SARS-CoV-2

<400> SEQUENCE: 6

Arg Val Gln Pro Thr Glu Ser Ile Val Arg Phe Pro Asn Ile Thr Asn
1               5                   10                  15

```
Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
 50                      55                  60

Ser Pro Thr Lys Leu Asn Asp Leu Cys Phe Thr Asn Val Tyr Ala Asp
 65                  70                  75                  80

Ser Phe Val Ile Arg Gly Asp Glu Val Arg Gln Ile Ala Pro Gly Gln
                 85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
            195                 200                 205

Pro Lys Lys Ser Thr Asn Leu Val Lys Asn Lys
        210                 215

<210> SEQ ID NO 7
<211> LENGTH: 223
<212> TYPE: PRT
<213> ORGANISM: Betacoronavirus/SARS-CoV-2

<400> SEQUENCE: 7

Arg Val Gln Pro Thr Glu Ser Ile Val Arg Phe Pro Asn Ile Thr Asn
 1               5                  10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
 50                      55                  60

Ser Pro Thr Lys Leu Asn Asp Leu Cys Phe Thr Asn Val Tyr Ala Asp
 65                  70                  75                  80

Ser Phe Val Ile Arg Gly Asp Glu Val Arg Gln Ile Ala Pro Gly Gln
                 85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
130                 135                 140

Pro Phe Glu Arg Asp Ile Ser Thr Glu Ile Tyr Gln Ala Gly Ser Thr
145                 150                 155                 160
```

Pro Cys Asn Gly Val Glu Gly Phe Asn Cys Tyr Phe Pro Leu Gln Ser
            165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
            195                 200                 205

Pro Lys Lys Ser Thr Asn Leu Val Lys Asn Lys Cys Val Asn Phe
            210                 215                 220

<210> SEQ ID NO 8
<211> LENGTH: 218
<212> TYPE: PRT
<213> ORGANISM: Betacoronavirus/Severe acute respiratory syndrome-
      related coronavirus

<400> SEQUENCE: 8

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
            35                  40                  45

Val Leu Tyr Asn Ser Thr Phe Phe Ser Thr Phe Lys Cys Tyr Gly Val
        50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
        115                 120                 125

Gly Asn Tyr Asn Tyr Lys Tyr Arg Tyr Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
                165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln
    210                 215

<210> SEQ ID NO 9
<211> LENGTH: 1458
<212> TYPE: DNA
<213> ORGANISM: Artificial Sequence
<220> FEATURE:
<223> OTHER INFORMATION: Synthesized

<400> SEQUENCE: 9
gaagcaaaac cttctggctc agttgtggaa caggctgaag gtgttgaatg tgattttcca      60
cctcttctgt ctggcacacc tcctcaggtt tataatttca gcgtttggt ttttaccaat     120 tgcaattata atcttaccaa attgctttca cttttttctg tgaatgattt tacttgtagt    180

```
caaatatctc cagcagcaat tgctagcaac tgttattctt cactgatttt ggattacttt      240
tcatacccac ttagtatgaa atccgatctc agtgttagtt ctgctggtcc aatatcccag      300
tttaattata aacagtcctt ttctaatccc acatgtttga ttttagcgac tgttcctcat      360
aaccttacta ctattactaa gcctcttaag tacagctata ttaacaagtg ctctcgtctt      420
ctttctgatg atcgtactga agtacctcag ttagtgaacg ctaatcaata ctcaccctgt      480
gtatccattg tccatccac tgtgtgggaa gacggtgatt attataggaa acaactatct       540
ccacttgaag gtggtggctg gcttgttgct agtggctcaa ctgttgccat gactgagcaa      600
ttacagatgg gctttggtat tacagttcaa tatggtacag acaccaatag tgtttgcccc      660
aagcttgaat ttgctaatga cacaaaaatt gcctctcaat taggcaattg cgtggaatat      720
ggcggctcag gcggctcaga agcaaaacct tctggctcag ttgtggaaca ggctgaaggt      780
gttgaatgtg atttttcacc tcttctgtct ggcacacctc ctcaggttta aatttcaag      840 cgtttggttt ttaccaattg caattataat cttaccaaat tgctttcact tttttctgtg      900
aatgatttta cttgtagtca aatatctcca gcagcaattg ctagcaactg ttattcttca      960
ctgattttgg attacttttc atacccactt agtatgaaat ccgatctcag tgttagttct      1020
gctggtccaa tatcccagtt taattataaa cagtcctttt ctaatcccac atgtttgatt      1080
ttagcgactt tcctcataa ccttactact attactaagc tcttaagta cagctatatt        1140 aacaagtgct ctcgtcttct ttctgatgat cgtactgaag tacctcagtt agtgaacgct      1200
aatcaatact caccctgtgt atccattgtc ccatccactg tgtgggaaga cggtgattat      1260
tataggaaac aactatctcc acttgaaggt ggtggctggc ttgttgctag tggctcaact      1320
gttgccatga ctgagcaatt acagatgggc tttggtatta cagttcaata tggtacagac      1380
accaatagtg tttgccccaa gcttgaattt gctaatgaca caaaaattgc ctctcaatta     1440
ggcaattgcg tggaatat                                                   1458

<210> SEQ ID NO 10
<211> LENGTH: 1449
<212> TYPE: DNA
<213> ORGANISM: Artificial Sequence
<220> FEATURE:
<223> OTHER INFORMATION: Synthesized

<400> SEQUENCE: 10
gaagcaaaac cttctggctc agttgtggaa caggctgaag gtgttgaatg tgattttca      60 cctcttctgt ctggcacacc tcctcaggtt tataatttca agcgtttggt ttttaccaat     120
tgcaattata atcttaccaa attgctttca cttttttctg tgaatgattt tacttgtagt     180
caaatatctc cagcagcaat tgctagcaac tgttattctt cactgatttt ggattacttt    240
tcatacccac ttagtatgaa atccgatctc agtgttagtt ctgctggtcc aatatcccag    300
tttaattata aacagtcctt ttctaatccc acatgtttga ttttagcgac tgttcctcat    360
aaccttacta ctattactaa gcctcttaag tacagctata ttaacaagtg ctctcgtctt    420
ctttctgatg atcgtactga agtacctcag ttagtgaacg ctaatcaata ctcaccctgt    480
gtatccattg tccatccac tgtgtgggaa gacggtgatt attataggaa acaactatct     540
ccacttgaag gtggtggctg gcttgttgct agtggctcaa ctgttgccat gactgagcaa    600
ttacagatgg gctttggtat tacagttcaa tatggtacag acaccaatag tgtttgcccc    660
aagcttgaat ttgctaatga cacaaaaatt gcctctcaat taggcaattg cgtggaatat    720
```

| | |
|---|---|
| ggcggctcag aagcaaaacc ttctggctca gttgtggaac aggctgaagg tgttgaatgt | 780 |
| gatttttcac ctcttctgtc tggcacacct cctcaggttt ataatttcaa gcgtttggtt | 840 |
| tttaccaatt gcaattataa tcttaccaaa ttgctttcac ttttttctgt gaatgatttt | 900 |
| acttgtagtc aaatatctcc agcagcaatt gctagcaact gttattcttc actgattttg | 960 |
| gattactttt catacccact tagtatgaaa tccgatctca gtgttagttc tgctggtcca | 1020 |
| atatcccagt ttaattataa acagtccttt tctaatccca catgtttgat tttagcgact | 1080 |
| gttcctcata accttactac tattactaag cctcttaagt acagctatat taacaagtgc | 1140 |
| tctcgtcttc tttctgatga tcgtactgaa gtacctcagt tagtgaacgc taatcaatac | 1200 |
| tcaccctgtg tatccattgt cccatccact gtgtgggaag acggtgatta ttataggaaa | 1260 |
| caactatctc cacttgaagg tggtggctgg cttgttgcta gtggctcaac tgttgccatg | 1320 |
| actgagcaat tacagatggg ctttggtatt acagttcaat atggtacaga caccaatagt | 1380 |
| gtttgcccca agcttgaatt tgctaatgac acaaaaattg cctctcaatt aggcaattgc | 1440 |
| gtggaatat | 1449 |

```
<210> SEQ ID NO 11
<211> LENGTH: 1440
<212> TYPE: DNA
<213> ORGANISM: Artificial Sequence
<220> FEATURE:
<223> OTHER INFORMATION: Synthesized

<400> SEQUENCE: 11
```

| | |
|---|---|
| gaagcaaaac cttctggctc agttgtggaa caggctgaag gtgttgaatg tgattttca | 60 |
| cctcttctgt ctggcacacc tcctcaggtt tataatttca agcgtttggt ttttaccaat | 120 |
| tgcaattata atcttaccaa attgctttca cttttttctg tgaatgattt tacttgtagt | 180 |
| caaatatctc cagcagcaat tgctagcaac tgttattctt cactgatttt ggattacttt | 240 |
| tcatacccac ttagtatgaa atccgatctc agtgttagtt ctgctggtcc aatatcccag | 300 |
| tttaattata acagtccttt ttctaatccc acatgtttga ttttagcgac tgttcctcat | 360 |
| aaccttacta ctattactaa gcctcttaag tacagctata ttaacaagtg ctctcgtctt | 420 |
| ctttctgatg atcgtactga agtacctcag ttagtgaacg ctaatcaata ctcaccctgt | 480 |
| gtatccattg tcccatccac tgtgtgggaa gacggtgatt attataggaa acaactatct | 540 |
| ccacttgaag gtggtggctg gcttgttgct agtggctcaa ctgttgccat gactgagcaa | 600 |
| ttacagatgg gctttggtat tacagttcaa tatggtacag acaccaatag tgtttgcccc | 660 |
| aagcttgaat ttgctaatga cacaaaaatt gcctctcaat taggcaattg cgtggaatat | 720 |
| gaagcaaaac cttctggctc agttgtggaa caggctgaag gtgttgaatg tgattttca | 780 |
| cctcttctgt ctggcacacc tcctcaggtt tataatttca agcgtttggt ttttaccaat | 840 |
| tgcaattata atcttaccaa attgctttca cttttttctg tgaatgattt tacttgtagt | 900 |
| caaatatctc cagcagcaat tgctagcaac tgttattctt cactgatttt ggattacttt | 960 |
| tcatacccac ttagtatgaa atccgatctc agtgttagtt ctgctggtcc aatatcccag | 1020 |
| tttaattata acagtccttt ttctaatccc acatgtttga ttttagcgac tgttcctcat | 1080 |
| aaccttacta ctattactaa gcctcttaag tacagctata ttaacaagtg ctctcgtctt | 1140 |
| ctttctgatg atcgtactga agtacctcag ttagtgaacg ctaatcaata ctcaccctgt | 1200 |
| gtatccattg tcccatccac tgtgtgggaa gacggtgatt attataggaa acaactatct | 1260 |
| ccacttgaag gtggtggctg gcttgttgct agtggctcaa ctgttgccat gactgagcaa | 1320 |

```
ttacagatgg gctttggtat tacagttcaa tatggtacag acaccaatag tgtttgcccc    1380
aagcttgaat tgctaatga cacaaaaatt gcctctcaat taggcaattg cgtggaatat    1440
```

<210> SEQ ID NO 12
<211> LENGTH: 1425
<212> TYPE: DNA
<213> ORGANISM: Artificial Sequence
<220> FEATURE:
<223> OTHER INFORMATION: Synthesized

<400> SEQUENCE: 12

```
gaagcaaaac cttctggctc agttgtggaa caggctgaag gtgttgaatg tgattttca     60 cctcttctgt ctggcacacc tcctcaggtt tataatttca agcgtttggt ttttaccaat    120
tgcaattata atcttaccaa attgctttca ctttttctg tgaatgattt tacttgtagt     180
caaatatctc cagcagcaat tgctagcaac tgttattctt cactgatttt ggattacttt    240
tcatacccac ttagtatgaa atccgatctc agtgttagtt ctgctggtcc aatatcccag    300
tttaattata aacagtcctt ttctaatccc acatgtttga ttttagcgac tgttcctcat    360
aaccttacta ctattactaa gcctcttaag tacagctata ttaacaagtg ctctcgtctt    420 cttttctgatg atcgtactga agtacctcag ttagtgaacg ctaatcaata ctcaccctgt    480
gtatccattg tcccatccac tgtgtgggaa gacggtgatt attataggaa acaactatct    540
ccacttgaag gtggtggctg gcttgttgct agtggctcaa ctgttgccat gactgagcaa    600
ttacagatgg gctttggtat tacagttcaa tatggtacag acaccaatag tgtttgcccc    660
aagcttgaat tgctaatga cacaaaaatt gcctctcaat taggcaatgg cggctcagaa    720
gcaaaacctt ctggctcagt tgtggaacag gctgaaggtg ttgaatgtga ttttcacct     780 cttctgtctg gcacacctcc tcaggtttat aatttcaagc gtttggtttt taccaattgc    840
aattataatc ttaccaaatt gctttcactt ttttctgtga atgattttac ttgtagtcaa    900
atatctccag cagcaattgc tagcaactgt tattcttcac tgattttgga ttacttttca    960
tacccactta gtatgaaatc cgatctcagt gttagttctg ctggtccaat atcccagttt    1020
aattataaac agtcctttc taatcccaca tgtttgattt tagcgactgt tcctcataac    1080
cttactacta ttactaagcc tcttaagtac agctatatta acaagtgctc tcgtcttctt    1140
tctgatgatc gtactgaagt acctcagtta gtgaacgcta atcaatactc accctgtgta    1200
tccattgtcc catccactgt gtgggaagac ggtgattatt ataggaaaca actatctcca    1260
cttgaaggtg gtggctggct tgttgctagt ggctcaactg ttgccatgac tgagcaatta    1320
cagatgggct ttggtattac agttcaatat ggtacagaca ccaatagtgt tgccccaag     1380 cttgaatttg ctaatgacac aaaaattgcc tctcaattag gcaat                    1425
```

<210> SEQ ID NO 13
<211> LENGTH: 1416
<212> TYPE: DNA
<213> ORGANISM: Artificial Sequence
<220> FEATURE:
<223> OTHER INFORMATION: Synthesized

<400> SEQUENCE: 13

```
gaagcaaaac cttctggctc agttgtggaa caggctgaag gtgttgaatg tgattttca     60 cctcttctgt ctggcacacc tcctcaggtt tataatttca agcgtttggt ttttaccaat    120
tgcaattata atcttaccaa attgctttca ctttttctg tgaatgattt tacttgtagt     180
```

| | |
|---|---|
| caaatatctc cagcagcaat tgctagcaac tgttattctt cactgatttt ggattacttt | 240 |
| tcatacccac ttagtatgaa atccgatctc agtgttagtt ctgctggtcc aatatcccag | 300 |
| tttaattata aacagtcctt ttctaatccc acatgtttga ttttagcgac tgttcctcat | 360 |
| aaccttacta ctattactaa gcctcttaag tacagctata ttaacaagtg ctctcgtctt | 420 |
| ctttctgatg atcgtactga agtacctcag ttagtgaacg ctaatcaata ctcaccctgt | 480 |
| gtatccattg tcccatccac tgtgtgggaa gacggtgatt attataggaa acaactatct | 540 |
| ccacttgaag gtggtggctg gcttgttgct agtggctcaa ctgttgccat gactgagcaa | 600 |
| ttacagatgg gctttggtat tacagttcaa tatggtacag acaccaatag tgtttgcccc | 660 |
| aagcttgaat ttgctaatga cacaaaaatt gcctctcaat taggcaatga agcaaaacct | 720 |
| tctggctcag ttgtgaaaca ggctgaaggt gttgaatgtg atttttcacc tcttctgtct | 780 |
| ggcacacctc ctcaggttta taatttcaag cgtttggttt ttaccaattg caattataat | 840 |
| cttaccaaat tgctttcact ttttttctgtg aatgatttta cttgtagtca aatatctcca | 900 |
| gcagcaattg ctagcaactg ttattcttca ctgattttgg attactttc ataccccactt | 960 |
| agtatgaaat ccgatctcag tgttagttct gctggtccaa tatcccagtt taattataaa | 1020 |
| cagtcctttt ctaatcccac atgtttgatt ttagcgactg ttcctcataa ccttactact | 1080 |
| attactaagc tcttaagta cagctatatt aacaagtgct ctcgtcttct ttctgatgat | 1140 |
| cgtactgaag tacctcagtt agtgaacgct aatcaatact caccctgtgt atccattgtc | 1200 |
| ccatccactg tgtgggaaga cggtgattat tataggaaac aactatctcc acttgaaggt | 1260 |
| ggtggctggc ttgttgctag tggctcaact gttgccatga ctgagcaatt acagatgggc | 1320 |
| tttggtatta cagttcaata tggtacagac accaatagtg tttgccccaa gcttgaattt | 1380 |
| gctaatgaca caaaaattgc ctctcaatta ggcaat | 1416 |

<210> SEQ ID NO 14
<211> LENGTH: 1293
<212> TYPE: DNA
<213> ORGANISM: Artificial Sequence
<220> FEATURE:
<223> OTHER INFORMATION: Synthesized

<400> SEQUENCE: 14

| | |
|---|---|
| gttgaatgtg atttttcacc tcttctgtct ggcacacctc ctcaggttta taatttcaag | 60 |
| cgtttggttt ttaccaattg caattataat cttaccaaat tgctttcact ttttctgtg | 120 |
| aatgatttta cttgtagtca aatatctcca gcagcaattg ctagcaactg ttattcttca | 180 |
| ctgattttgg attactttc ataccccactt agtatgaaat ccgatctcag tgttagttct | 240 |
| gctggtccaa tatcccagtt taattataaa cagtcctttt ctaatcccac atgtttgatt | 300 |
| ttagcgactg ttcctcataa ccttactact attactaagc tcttaagta cagctatatt | 360 |
| aacaagtgct ctcgtcttct ttctgatgat cgtactgaag tacctcagtt agtgaacgct | 420 |
| aatcaatact caccctgtgt atccattgtc ccatccactg tgtgggaaga cggtgattat | 480 |
| tataggaaac aactatctcc acttgaaggt ggtggctggc ttgttgctag tggctcaact | 540 |
| gttgccatga ctgagcaatt acagatgggc tttggtatta cagttcaata tggtacagac | 600 |
| accaatagtg tttgccccaa gcttggcggc tcaggcggct caggcggctc aggcggctca | 660 |
| ggcggctcag ttgaatgtga tttttcacct cttctgtctg gcacacctcc tcaggtttat | 720 |
| aatttcaagc gtttggtttt taccaattgc aattataatc ttaccaaatt gctttcactt | 780 |
| ttttctgtga atgattttac ttgtagtcaa atatctccag cagcaattgc tagcaactgt | 840 |

```
tattcttcac tgattttgga ttacttttca tacccactta gtatgaaatc cgatctcagt    900
gttagttctg ctggtccaat atcccagttt aattataaac agtccttttc taatcccaca    960
tgtttgattt tagcgactgt tcctcataac cttactacta ttactaagcc tcttaagtac   1020
agctatatta acaagtgctc tcgtcttctt tctgatgatc gtactgaagt acctcagtta   1080
gtgaacgcta atcaatactc accctgtgta tccattgtcc catccactgt gtgggaagac   1140
ggtgattatt ataggaaaca actatctcca cttgaaggtg gtggctggct tgttgctagt   1200
ggctcaactg ttgccatgac tgagcaatta cagatgggct ttggtattac agttcaatat   1260
ggtacagaca ccaatagtgt ttgccccaag ctt                                1293
```

<210> SEQ ID NO 15
<211> LENGTH: 1284
<212> TYPE: DNA
<213> ORGANISM: Artificial Sequence
<220> FEATURE:
<223> OTHER INFORMATION: Synthesized

<400> SEQUENCE: 15

```
gttgaatgtg attttcacc tcttctgtct ggcacacctc ctcaggttta aatttcaag      60 cgtttggttt ttaccaattg caattataat cttaccaaat tgctttcact ttttctgtg    120 aatgatttta cttgtagtca aatatctcca gcagcaattg ctagcaactg ttattcttca    180
ctgattttgg attactttc atacccactt agtatgaaat ccgatctcag tgttagttct    240
gctggtccaa tatcccagtt taattataaa cagtccttt ctaatcccac atgtttgatt    300
ttagcgactg ttcctcataa ccttactact attactaagc ctcttaagta cagctatatt    360
aacaagtgct ctcgtcttct ttctgatgat cgtactgaag tacctcagtt agtgaacgct    420
aatcaatact caccctgtgt atccattgtc ccatccactg tgtgggaaga cggtgattat    480
tataggaaac aactatctcc acttgaaggt ggtggctggc ttgttgctag tggctcaact    540
gttgccatga ctgagcaatt acagatgggc tttggtatta cagttcaata tggtacagac    600
accaatagtg tttgccccaa gcttggcggc tcaggcggct caggcggctc aggcggctca    660
gttgaatgtg attttcacc tcttctgtct ggcacacctc ctcaggttta aatttcaag    720 cgtttggttt ttaccaattg caattataat cttaccaaat tgctttcact ttttctgtg    780 aatgatttta cttgtagtca aatatctcca gcagcaattg ctagcaactg ttattcttca    840
ctgattttgg attactttc atacccactt agtatgaaat ccgatctcag tgttagttct    900
gctggtccaa tatcccagtt taattataaa cagtccttt ctaatcccac atgtttgatt    960
ttagcgactg ttcctcataa ccttactact attactaagc ctcttaagta cagctatatt   1020
aacaagtgct ctcgtcttct ttctgatgat cgtactgaag tacctcagtt agtgaacgct   1080
aatcaatact caccctgtgt atccattgtc ccatccactg tgtgggaaga cggtgattat   1140
tataggaaac aactatctcc acttgaaggt ggtggctggc ttgttgctag tggctcaact   1200
gttgccatga ctgagcaatt acagatgggc tttggtatta cagttcaata tggtacagac   1260
accaatagtg tttgccccaa gctt                                          1284
```

<210> SEQ ID NO 16
<211> LENGTH: 1275
<212> TYPE: DNA
<213> ORGANISM: Artificial Sequence
<220> FEATURE:
<223> OTHER INFORMATION: Synthesized

<400> SEQUENCE: 16

```
gttgaatgtg attttcacc tcttctgtct ggcacacctc ctcaggttta taatttcaag      60
cgtttggttt ttaccaattg caattataat cttaccaaat tgctttcact ttttctgtg     120
aatgatttta cttgtagtca aatatctcca gcagcaattg ctagcaactg ttattcttca    180
ctgattttgg attactttc atcccactt agtatgaaat ccgatctcag tgttagttct     240
gctggtccaa tatcccagtt taattataaa cagtccttt ctaatcccac atgtttgatt    300
ttagcgactg ttcctcataa ccttactact attactaagc ctcttaagta cagctatatt   360
aacaagtgct ctcgtcttct ttctgatgat cgtactgaag tacctcagtt agtgaacgct   420
aatcaatact caccctgtgt atccattgtc ccatccactg tgtgggaaga cggtgattat   480
tataggaaac aactatctcc acttgaaggt ggtggctggc ttgttgctag tggctcaact   540
gttgccatga ctgagcaatt acagatgggc tttggtatta cagttcaata tggtacagac   600
accaatagtg tttgccccaa gcttggcggc tcaggcggct caggcggctc agttgaatgt   660
gattttcac ctcttctgtc tggcacacct cctcaggttt ataatttcaa gcgtttggtt   720
tttaccaatt gcaattataa tcttaccaaa ttgctttcac ttttctgt gaatgatttt    780
acttgtagtc aaatatctcc agcagcaatt gctagcaact gttattcttc actgattttg   840
gattactttt catcccact agtatgaaa tccgatctca gtgttagttc tgctggtcca    900
atatcccagt ttaattataa acagtccttt tctaatccca catgtttgat tttagcgact   960
gttcctcata accttactac tattactaag cctcttaagt acagctatat taacaagtgc  1020
tctcgtcttc tttctgatga tcgtactgaa gtacctcagt tagtgaacgc taatcaatac  1080
tcaccctgtg tatccattgt cccatccact gtgtgggaag acggtgatta ttataggaaa  1140
caactatctc cacttgaagg tggtggctgg cttgttgcta gtggctcaac tgttgccatg  1200
actgagcaat tacagatggg ctttggtatt acagttcaat atggtacaga caccaatagt  1260
gtttgcccca agctt                                                   1275
```

<210> SEQ ID NO 17
<211> LENGTH: 1257
<212> TYPE: DNA
<213> ORGANISM: Artificial Sequence
<220> FEATURE:
<223> OTHER INFORMATION: Synthesized

<400> SEQUENCE: 17

```
gttgaatgtg attttcacc tcttctgtct ggcacacctc ctcaggttta taatttcaag      60
cgtttggttt ttaccaattg caattataat cttaccaaat tgctttcact ttttctgtg     120
aatgatttta cttgtagtca aatatctcca gcagcaattg ctagcaactg ttattcttca    180
ctgattttgg attactttc atcccactt agtatgaaat ccgatctcag tgttagttct     240
gctggtccaa tatcccagtt taattataaa cagtccttt ctaatcccac atgtttgatt    300
ttagcgactg ttcctcataa ccttactact attactaagc ctcttaagta cagctatatt   360
aacaagtgct ctcgtcttct ttctgatgat cgtactgaag tacctcagtt agtgaacgct   420
aatcaatact caccctgtgt atccattgtc ccatccactg tgtgggaaga cggtgattat   480
tataggaaac aactatctcc acttgaaggt ggtggctggc ttgttgctag tggctcaact   540
gttgccatga ctgagcaatt acagatgggc tttggtatta cagttcaata tggtacagac   600
accaatagtg tttgccccaa gcttggcggc tcagttgaat gtgattttc acctcttctg   660
tctggcacac ctcctcaggt ttataatttc aagcgtttgg ttttaccaa ttgcaattat   720
```

```
aatcttacca aattgctttc acttttttct gtgaatgatt ttacttgtag tcaaatatct    780
ccagcagcaa ttgctagcaa ctgttattct tcactgattt tggattactt ttcataccca    840
cttagtatga atccgatct cagtgttagt tctgctggtc caatatccca gtttaattat     900
aaacagtcct tttctaatcc cacatgtttg attttagcga ctgttcctca taaccttact    960
actattacta agcctcttaa gtacagctat attaacaagt gctctcgtct tctttctgat   1020
gatcgtactg aagtacctca gttagtgaac gctaatcaat actcaccctg tgtatccatt   1080
gtcccatcca ctgtgtggga agacggtgat tattatagga acaactatc tccacttgaa   1140 ggtggtggct ggcttgttgc tagtggctca actgttgcca tgactgagca attacagatg   1200
ggctttggta ttacagttca atatggtaca gacaccaata gtgtttgccc caagctt     1257
```

<210> SEQ ID NO 18
<211> LENGTH: 1248
<212> TYPE: DNA
<213> ORGANISM: Artificial Sequence
<220> FEATURE:
<223> OTHER INFORMATION: Synthesized

<400> SEQUENCE: 18

```
gttgaatgtg attttcacc tcttctgtct ggcacacctc ctcaggttta aatttcaag      60 cgtttggttt ttaccaattg caattataat cttaccaaat tgcttcact tttttctgtg    120 aatgatttta cttgtagtca aatatctcca gcagcaattg ctagcaactg ttattcttca   180
ctgattttgg attacttttc atacccactt agtatgaaat ccgatctcag tgttagttct   240
gctggtccaa tatcccagtt taattataaa cagtcctttt ctaatcccac atgtttgatt   300
ttagcgactg ttcctcataa ccttactact attactaagc tcttaagta cagctatatt    360 aacaagtgct ctcgtcttct ttctgatgat cgtactgaag tacctcagtt agtgaacgct   420
aatcaatact caccctgtgt atccattgtc ccatccactg tgtgggaaga cggtgattat   480
tataggaaac aactatctcc acttgaaggt ggtggctggc ttgttgctag tggctcaact   540
gttgccatga ctgagcaatt acagatgggc tttggtatta cagttcaata tggtacagac   600
accaatagtg tttgccccaa gcttgttgaa tgtgattttt cacctcttct gtctggcaca   660
cctcctcagg tttataattt caagcgtttg gtttttacca attgcaatta taatcttacc   720
aaattgcttt cacttttttc tgtgaatgat tttacttgta gtcaaatatc tccagcagca   780
attgctagca actgttattc ttcactgatt ttggattact tttcataccc acttagtatg   840
aaatccgatc tcagtgttag ttctgctggt ccaatatccc agtttaatta taaacagtcc   900
ttttctaatc ccacatgttt gattttagcg actgttcctc ataaccttac tactattact   960
aagcctctta gtacagcta tattaacaag tgctctcgtc ttctttctga tgatcgtact   1020
gaagtacctc agttagtgaa cgctaatcaa tactcaccct gtgtatccat tgtcccatcc   1080
actgtgtggg aagacggtga ttattatagg aacaactat ctccacttga aggtggtggc   1140
tggcttgttg ctagtggctc aactgttgcc atgactgagc aattacagat gggctttggt   1200
attacagttc aatatggtac agacaccaat agtgtttgcc ccaagctt                1248
```

<210> SEQ ID NO 19
<211> LENGTH: 1272
<212> TYPE: DNA
<213> ORGANISM: Artificial Sequence
<220> FEATURE:
<223> OTHER INFORMATION: Synthesized

<400> SEQUENCE: 19

```
agagtgcaac ctacagaatc aatcgtgaga tttcctaaca tcacaaacct ttgcccttc     60
ggcgaggtgt ttaacgcaac aagatttgca tcagtgtacg catggaacag aaagcgtata   120
tcaaactgcg tggcagatta ctcagtgctt tacaactcag catcattcag tacgtttaaa   180
tgctacggag tgtcacctac aaagctaaat gatctttgct ttacaaacgt gtacgcagat   240
tcatttgtga tcagaggaga tgaagtgaga caaatcgcac tggacaaac aggaaagatt    300
gccgattaca actacaaact tcctgatgat ttcaccggct gcgtgatcgc atggaactca   360
aacaaccttg attcaaaggt aggtggtaat tataattatt tgtataggct ctttcgtaag   420
agcaacttaa agccatttga gcgagatatc tcaacagaaa tctaccaagc aggatcaaca   480
ccttgcaacg gagtggaagg atttaactgc tactttcctc ttcaatcata cggatttcaa   540
cctacaaacg gagtgggata ccaaccttac agagtggtgg tgctttcatt tgaacttctt   600
cacgcacctg caacagtgtg cggacctaag aagagcagag tgcaacctac agaatcaatc   660
gtgagatttc ctaacatcac aaaccttgc cctttcggcg aggtgtttaa cgcaacaaga   720
tttgcatcag tgtacgcatg gaacagaaag cgtatatcaa actgcgtggc agattactca   780
gtgctttaca actcagcatc attcagtacg tttaaatgct acggagtgtc acctacaaag   840
ctaaatgatc tttgctttac aaacgtgtac gcagattcat ttgtgatcag aggagatgaa   900
gtgagacaaa tcgcacctgg acaaacagga aagattgccg attacaacta caaacttcct   960
gatgatttca ccggctgcgt gatcgcatgg aactcaaaca accttgattc aaaggtaggt  1020
ggtaattata attatttgta taggctcttt cgtaagagca acttaaagcc atttgagcga  1080
gatatctcaa cagaaatcta ccaagcagga tcaacacctt gcaacggagt ggaaggattt  1140
aactgctact ttcctcttca atcatacgga tttcaaccta caaacggagt gggataccaa  1200
ccttacagag tggtggtgct ttcatttgaa cttcttcacg cacctgcaac agtgtgcgga  1260
cctaagaaga gc                                                      1272
```

<210> SEQ ID NO 20
<211> LENGTH: 1314
<212> TYPE: DNA
<213> ORGANISM: Artificial Sequence
<220> FEATURE:
<223> OTHER INFORMATION: Synthesized

<400> SEQUENCE: 20

```
agagtgcaac ctacagaatc aatcgtgaga tttcctaaca tcacaaacct ttgcccttc     60
ggcgaggtgt ttaacgcaac aagatttgca tcagtgtacg catggaacag aaagcgtata   120
tcaaactgcg tggcagatta ctcagtgctt tacaactcag catcattcag tacgtttaaa   180
tgctacggag tgtcacctac aaagctaaat gatctttgct ttacaaacgt gtacgcagat   240
tcatttgtga tcagaggaga tgaagtgaga caaatcgcac tggacaaac aggaaagatt    300
gccgattaca actacaaact tcctgatgat ttcaccggct gcgtgatcgc atggaactca   360
aacaaccttg attcaaaggt aggtggtaat tataattatt tgtataggct ctttcgtaag   420
agcaacttaa agccatttga gcgagatatc tcaacagaaa tctaccaagc aggatcaaca   480
ccttgcaacg gagtggaagg atttaactgc tactttcctc ttcaatcata cggatttcaa   540
cctacaaacg gagtgggata ccaaccttac agagtggtgg tgctttcatt tgaacttctt   600
cacgcacctg caacagtgtg cggacctaag aagagcacga accttgtgaa gaataagaga   660
gtgcaaccta cagaatcaat cgtgagattt cctaacatca caaaccttgc cctttcggc    720
```

```
gaggtgttta acgcaacaag atttgcatca gtgtacgcat ggaacagaaa gcgtatatca        780
aactgcgtgg cagattactc agtgctttac aactcagcat cattcagtac gtttaaatgc        840
tacggagtgt cacctacaaa gctaaatgat ctttgcttta caaacgtgta cgcagattca        900
tttgtgatca gaggagatga agtgagacaa atcgcacctg acaaacagg  aaagattgcc        960 gattacaact acaaacttcc tgatgatttc accggctgcg tgatcgcatg gaactcaaac       1020
aaccttgatt caaggtagg  tggtaattat aattatttgt ataggctctt tcgtaagagc       1080
aacttaaagc catttgagcg agatatctca acagaaatct accaagcagg atcaacacct       1140
tgcaacggag tggaaggatt taactgctac tttcctcttc aatcatacgg atttcaacct       1200
acaaacggag tgggatacca accttacaga gtggtggtgc tttcatttga acttcttcac       1260
gcacctgcaa cagtgtgcgg acctaagaag agcacgaacc ttgtgaagaa taag            1314
```

<210> SEQ ID NO 21
<211> LENGTH: 1338
<212> TYPE: DNA
<213> ORGANISM: Artificial Sequence
<220> FEATURE:
<223> OTHER INFORMATION: Synthesized

<400> SEQUENCE: 21

```
agagtgcaac ctacagaatc aatcgtgaga tttcctaaca tcacaaacct ttgcccttc         60 ggcgaggtgt ttaacgcaac aagatttgca tcagtgtacg catggaacag aaagcgtata       120
tcaaactgcg tggcagatta ctcagtgctt tacaactcag catcattcag tacgtttaaa       180
tgctacggag tgtcacctac aaagctaaat gatctttgct ttacaaacgt gtacgcagat       240
tcatttgtga tcagaggaga tgaagtgaga caaatcgcac ctggacaaac aggaaagatt       300
gccgattaca actacaaact tcctgatgat ttcaccggct gcgtgatcgc atggaactca       360
aacaaccttg attcaaaggt aggtggtaat tataattatt tgtataggct ctttcgtaag       420
agcaacttaa agccatttga gcgagatatc tcaacagaaa tctaccaagc aggatcaaca       480
ccttgcaacg gagtggaagg atttaactgc tactttcctc ttcaatcata cggatttcaa       540
cctacaaacg gagtgggata ccaaccttac agagtggtgg tgctttcatt tgaacttctt       600
cacgcacctg caacagtgtg cggacctaag aagagcacga accttgtgaa gaataagtgc       660 gtgaactttta gagtgcaacc tacagaatca atcgtgagat ttcctaacat cacaaacctt       720 tgcccttcg gcgaggtgtt taacgcaaca gatttgcat cagtgtacgc atggaacaga        780
aagcgtatat caaactgcgt ggcagattac tcagtgcttt acaactcagc atcattcagt       840
acgtttaaat gctacggagt gtcacctaca aagctaaatg atctttgctt tacaaacgtg       900
tacgcagatt catttgtgat cagaggagat gaagtgagac aaatcgcacc tggacaaaca       960
ggaaagattg ccgattacaa ctacaaactt cctgatgatt tcaccggctg cgtgatcgca      1020
tggaactcaa acaaccttga ttcaaaggta ggtggtaatt ataattattt gtataggctc      1080
tttcgtaaga gcaacttaaa gccatttgag cgagatatct caacagaaat ctaccaagca      1140
ggatcaacac cttgcaacgg agtggaagga tttaactgct actttcctct tcaatcatac      1200
ggatttcaac ctacaaacgg agtgggatac caaccttaca gagtggtggt gctttcattt      1260
gaacttcttc acgcacctgc aacagtgtgc ggacctaaga agagcacgaa ccttgtgaag      1320
aataagtgcg tgaacttt                                                    1338
```

<210> SEQ ID NO 22

```
<211> LENGTH: 669
<212> TYPE: DNA
<213> ORGANISM: Artificial Sequence
<220> FEATURE:
<223> OTHER INFORMATION: Synthesized

<400> SEQUENCE: 22
agagtgcaac ctacagaatc aatcgtgaga tttcctaaca tcacaaacct ttgcccttcc      60
ggcgaggtgt ttaacgcaac aagatttgca tcagtgtacg catggaacag aaagcgtata     120
tcaaactgcg tggcagatta ctcagtgctt tacaactcag catcattcag tacgtttaaa     180
tgctacggag tgtcacctac aaagctaaat gatctttgct ttacaaacgt gtacgcagat     240
tcatttgtga tcagaggaga tgaagtgaga caaatcgcac ctggacaaac aggaaagatt     300
gccgattaca actacaaact tcctgatgat ttcaccggct gcgtgatcgc atggaactca     360
aacaaccttg attcaaggt aggtggtaat tataattatt tgtataggct ctttcgtaag     420
agcaacttaa agccatttga gcagatatc tcaacagaaa tctaccaagc aggatcaaca     480
ccttgcaacg gagtggaagg atttaactgc tactttcctc ttcaatcata cggatttcaa     540
cctacaaacg gagtgggata ccaaccttac agagtggtgg tgctttcatt tgaacttctt     600
cacgcacctg caacagtgtg cggacctaag aagagcacga accttgtgaa gaataagtgc     660
gtgaacttt                                                            669

<210> SEQ ID NO 23
<211> LENGTH: 1308
<212> TYPE: DNA
<213> ORGANISM: Artificial Sequence
<220> FEATURE:
<223> OTHER INFORMATION: Synthesized

<400> SEQUENCE: 23
agggtagttc cctccggtga cgtcgttcgt ttcccaaata taacaaacct ctgtccatt      60 ggagaagtat ttaacgcgac taaatttcct agcgtatacg cctgggaaag gaagaaaata    120
agcaattgtg ttgcggacta ttccgtacta tataattcga cttttcttcag caccttcaag    180 tgttatggag tatcggctac taaactcaac gacttgtgtt ctcgaacgt ctacgcggat    240 tctttcgttg tcaaaggaga tgatgtgaga cagatagcac ctggacaaac cggtgttatc    300
gctgattaca actacaaact tcccgacgac tttatgggct gtgtactagc ctggaatact    360
cggaatattg acgccacctc taccggtaat tataattata agtataggta tttacgtcat    420
gggaaactga ggccgtttga aagggacatt tccaatgtac catttagtcc agacgggaaa    480
ccatgcacgc cgccagcact caattgttat tggcccctaa acgactatgg ttttttatacg    540 acgaccggaa ttgggtacca accctaccgt gttgtagtgc tgagctttga acttctaaat    600
gcgcccgcta ctgtctgtgg tccgaagcta tcgactgacc tcataaagaa tcagcgtgtt    660
gtcccatccg gtgacgttgt ccggtttcct aacatcacaa acttgtgtcc ctttggcgaa    720
gtcttcaatg ctaccaaatt tcccagcgtc tacgcgtggg aaagaaagaa aatatcaaat    780
tgtgttgccg actattccgt cctatataat agcacgttct tctcgacgtt caagtgttat    840
ggtgtctctg ctacgaaact taacgactta tgtttctcaa acgtgtacgc agattctttc    900
gtagttaaag gtgatgatgt gaggcagatt gcgcccggac aaacaggagt aatcgccgat    960
tacaactaca aactcccgga cgactttatg gggtgtgtgt tagcttggaa tacgaggaat   1020
atagacgcca cgagtaccgg gaattataat tataagtatc gctatctccg acatggcaaa   1080
ctcaggccat ttgaacgcga cattagcaat gttccattct ctccggacgg caaaccgtgc   1140
```

```
actccaccgg ctttaaattg ttattggccg ttaaacgact atggctttta tacaacgacg    1200
ggaatagggt accaacctta cagagtagta gtactaagtt tcgagctatt aaatgcgccg    1260
gccaccgtat gtgggcccaa gctatcgacg gacctaatca agaatcag                1308
```

```
<210> SEQ ID NO 24
<211> LENGTH: 720
<212> TYPE: DNA
<213> ORGANISM: Artificial Sequence
<220> FEATURE:
<223> OTHER INFORMATION: Synthesized

<400> SEQUENCE: 24
gaagcaaaac cttctggctc agttgtggaa caggctgaag gtgttgaatg tgattttca      60 cctcttctgt ctggcacacc tcctcaggtt tataatttca agcgtttggt ttttaccaat    120
tgcaattata atcttaccaa attgctttca cttttttctg tgaatgattt tacttgtagt    180
caaatatctc cagcagcaat tgctagcaac tgttattctt cactgatttt ggattacttt    240
tcatacccac ttagtatgaa atccgatctc agtgttagtt ctgctggtcc aatatcccag    300
tttaattata acagtccttt tctaatccc acatgtttga ttttagcgac tgttcctcat     360
aaccttacta ctattactaa gcctcttaag tacagctata ttaacaagtg ctctcgtctt    420
ctttctgatg atcgtactga agtacctcag ttagtgaacg ctaatcaata ctcaccctgt    480
gtatccattg tcccatccac tgtgtgggaa gacggtgatt attataggaa acaactatct    540
ccacttgaag gtggtggctg gcttgttgct agtggctcaa ctgttgccat gactgagcaa    600
ttacagatgg gctttggtat tacagttcaa tatggtacag acaccaatag tgtttgcccc    660
aagcttgaat tgctaatgaa cacaaaaatt gcctctcaat taggcaattg cgtggaatat    720
```

```
<210> SEQ ID NO 25
<211> LENGTH: 633
<212> TYPE: DNA
<213> ORGANISM: Artificial Sequence
<220> FEATURE:
<223> OTHER INFORMATION: Synthesized

<400> SEQUENCE: 25
gaaggtgttg aatgtgattt ttcacctctt ctgtctggca cacctcctca ggtttataat     60
ttcaagcgtt tggtttttac caattgcaat tataatctta ccaaattgct ttcacttttt    120
tctgtgaatg attttacttg tagtcaaata tctccagcag caattgctag caactgttat    180
tcttcactga ttttggatta cttttcatac ccacttagta tgaaatccga tctcagtgtt    240
agttctgctg gtccaatatc ccagtttaat tataaacagt ccttttctaa tcccacatgt    300
ttgattttag cgactgttcc tcataacctt actactatta ctaagcctct taagtacagc    360
tatattaaca agtgctctcg tcttctttct gatgatcgta ctgaagtacc tcagttagtg    420
aacgctaatc aatactcacc ctgtgtatcc attgtcccat ccactgtgtg ggaagacggt    480
gattattata ggaaacaact atctccactt gaaggtggtg gctggcttgt tgctagtggc    540
tcaactgttg ccatgactga gcaattacag atgggctttg gtattacagt tcaatatggt    600
acagacacca atagtgtttg cccccaagctt gaa                                633
```

```
<210> SEQ ID NO 26
<211> LENGTH: 222
<212> TYPE: PRT
<213> ORGANISM: Betacoronavirus/Severe acute respiratory syndrome-
    related coronavirus
```

<400> SEQUENCE: 26

```
Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45

Val Leu Tyr Asn Ser Thr Phe Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
                85                  90                  95

Thr Gly Val Ile Ala Asp Tyr Asn Tyr Lys Leu Pro Asp Asp Phe Met
                100                 105                 110

Gly Cys Val Leu Ala Trp Asn Thr Arg Asn Ile Asp Ala Thr Ser Thr
            115                 120                 125

Gly Asn Tyr Asn Tyr Lys Tyr Arg Tyr Leu Arg His Gly Lys Leu Arg
130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
                165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
    210                 215                 220
```

<210> SEQ ID NO 27
<211> LENGTH: 666
<212> TYPE: DNA
<213> ORGANISM: Artificial Sequence
<220> FEATURE:
<223> OTHER INFORMATION: Synthesized

<400> SEQUENCE: 27

```
cgtgttgtcc catccggtga cgttgtccgg tttcctaaca tcacaaactt gtgtcccttt      60
ggcgaagtct tcaatgctac caaatttccc agcgtctacg cgtgggaaag aaagaaaata     120
tcaaattgtg ttgccgacta ttccgtccta tataatagca cgttcttctc gacgttcaag     180
tgttatggtg tctctgctac gaaacttaac gacttatgtt tctcaaacgt gtacgcagat     240
tctttcgtag ttaaaggtga tgatgtgagg cagattgcgc ccggacaaac aggagtaatc     300
gccgattaca actacaaact cccggacgac tttatgggt gtgtgttagc ttggaatacg      360
aggaatatag acgccacgag taccgggaat tataattata agtatcgcta tctccgacat     420
ggcaaactca ggccatttga acgcgacatt agcaatgttc cattctctcc ggacggcaaa     480
ccgtgcactc caccggcttt aaattgttat tggccgttaa acgactatgg cttttataca     540
acgacgggaa tagggtacca accttacaga gtagtagtac taagtttcga gctattaaat     600
gcgccggcca ccgtatgtgg gcccaagcta tcgacggacc taatcaagaa tcagtgtgtt     660
aattcc                                                                666
```